United States Patent
Neagle et al.

(10) Patent No.: US 11,320,380 B2
(45) Date of Patent: May 3, 2022

(54) OPTICAL MODULE WITH THREE OR MORE COLOR FLUORESCENT LIGHT SOURCES AND METHODS FOR USE THEREOF

(71) Applicant: Sartorius BioAnalytical Instruments, Inc., Bohemia, NY (US)

(72) Inventors: Bradley Neagle, Ann Arbor, MI (US); Alan Riggs, Ann Arbor, MI (US); Michael Kusner, Ann Arbor, MI (US); Kyle Schutte, Ann Arbor, MI (US); Eric Endsley, Saline, MI (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 0 days.

(21) Appl. No.: 16/854,756

(22) Filed: Apr. 21, 2020

(65) Prior Publication Data
US 2021/0325309 A1    Oct. 21, 2021

(51) Int. Cl.
*G01N 21/64* (2006.01)
*C12M 1/00* (2006.01)
*G06T 7/00* (2017.01)

(52) U.S. Cl.
CPC ......... *G01N 21/6486* (2013.01); *C12M 41/14* (2013.01); *G01N 21/6428* (2013.01); *G06T 7/0012* (2013.01); *G01N 2021/6421* (2013.01); *G01N 2021/6463* (2013.01); *G06T 2207/30024* (2013.01)

(58) Field of Classification Search
None
See application file for complete search history.

(56) References Cited

U.S. PATENT DOCUMENTS

| 2013/0102481 A1* | 4/2013 | McCollum ........... G01N 21/253 506/9 |
| 2016/0216503 A1* | 7/2016 | Kim ................... G02B 13/0095 |
| 2017/0058343 A1* | 3/2017 | Quintel ................ G01J 3/4406 |

(Continued)

FOREIGN PATENT DOCUMENTS

| GB | 2423151 B | 5/2007 |
| WO | 2019096974 A1 | 5/2019 |

OTHER PUBLICATIONS

Delivering Fast and Sharp Live-Cell Imaging to Your Incubator. Cellcyte brochure, 8 pp., Retrieved on Apr. 21, 2020.

*Primary Examiner* — Hugh Maupin
(74) *Attorney, Agent, or Firm* — McDonnell Boehnen Hulbert & Berghoff LLP

(57) ABSTRACT

An imaging apparatus is provided to facilitate epifluorescent imaging of three (or more) color channels and to perform phase contrast and/or bright field imaging of samples without manual adjustment of the imaging apparatus. This allows for automated imaging, over extended periods of time, of a plurality of samples by a device located inside an incubator without disturbing the incubator environment to manually adjust the apparatus. Also provided are embodiments to facilitate user swapping of removable optical modules and/or transillumination modules to allow the imaging apparatus to be adapted to different combinations of assays and/or fluorescent indicators so as to increase the variety of experiments and/or fluorescent dyes that can be imaged using the imaging apparatus.

24 Claims, 16 Drawing Sheets

(56) References Cited

U.S. PATENT DOCUMENTS

2018/0196246 A1* 7/2018 Bares ............... G01J 3/0208
2019/0271592 A1* 9/2019 Gray ............... G01N 21/6458
2021/0333532 A1* 10/2021 Whoriskey ............ G02B 21/16

* cited by examiner

OPTICAL MODULE WITH THREE OR MORE COLOR FLUORESCENT LIGHT SOURCES AND METHODS FOR USE THEREOF

BACKGROUND

Live cell biological samples can be microscopically imaged in a variety of ways in order to assess the growth, metabolism, morphology, or other properties of the sample at one or more points in time. This microscopic imaging can include fluorescence imaging, wherein fluorophores in the sample are excited by light at excitation wavelength(s) of the fluorophores, causing them to fluorescently emit light at emission wavelength(s) of the fluorophores. In epifluorescence imaging, the excitation light is provided via the same objective that is used to collect to the emission light.

Achieving multi-channel fluorescence imaging often involves moving different filter sets, and occasionally excitation light sources, into position each time a fluorescence image is acquired for a particular emission wavelength. Such an arrangement, however, results in a larger, slower, more costly, and less reliable system due to the need to physically move components.

SUMMARY

In a first aspect, an example optical module for imaging fluorophores in a live-cell biological sample is disclosed. The optical module includes (a) a first light source configured to emit a first light in a first band of excitation wavelengths, (b) a first filter arranged in a first optical path of the first light source, the first filter is configured to pass light in one or more wavelengths and to reflect light in one or more wavelengths, (c) a second light source configured to emit a second light in a second band of excitation wavelengths, (d) a second filter arranged in a second optical path of the second light source, the second filter is configured to pass light in one or more wavelengths and to reflect light in one or more wavelengths, (e) a third light source configured to emit a third light in a third band of excitation wavelengths, (f) a third filter arranged in a third optical path of the third light source, the third filter is configured to pass light in one or more wavelengths and to reflect light in one or more wavelengths, wherein the first optical path, the second optical path, and the third optical path converge along a primary transmission optical path configured to be directed toward the live-cell biological sample, and (g) an emission filter arranged in a primary emission optical path for light emitted by the fluorophores in the live-cell biological sample, where the primary emission optical path is configured to terminate at an imaging sensor, where the emission filter is configured to pass light in a first band, a second band and a third band of emission wavelengths and is configured to reflect light in the first band, the second band and the third band of excitation wavelengths.

In a second aspect, an example system for assaying live-cell biological samples is disclosed. The system includes (a) the optical module according to the first aspect of the disclosure, (b) a fluorescence microscope removably coupled to the optical module, where the fluorescence microscope has at least one objective, (c) the imaging sensor arranged in the emission path for light emitted by the fluorophores in the live-cell biological sample from the objective, and (d) a phase lamp removably coupled to the fluorescence microscope and arranged at a terminating end of the primary transmission optical path.

In a third aspect, an example method for imaging fluorophores in live-cell biological samples is disclosed. The method includes: (i) aligning a first biological sample and a fluorescence microscope such that the first biological sample is located within a field of view of the fluorescence microscope, wherein the first biological sample contains (a) a first fluorophore that emits light in a first band of emission wavelengths in response to illumination by light in first band of excitation wavelengths, (b) a second fluorophore that emits light in a second band of emission wavelengths in response to illumination by light in second band of excitation wavelengths, and (c) a third fluorophore that emits light in a third band of emission wavelengths in response to illumination by light in third band of excitation wavelengths; (ii) obtaining a set of images of the first biological sample using the fluorescent microscope, wherein the images of the set of images differ with respect to focus setting; (iii) determining, based on the set of images, first, second, and third in-focus settings for the first, second, and third bands of emission wavelengths, respectively; (iv) during a first period of time, using a first light source to illuminate the first biological sample with light in the first band of excitation wavelengths and operating the fluorescence microscope according to the first in-focus setting to obtain, via an image sensor of the fluorescence microscope, a first image of light in the first band of emission wavelengths; (v) during a second period of time, using a second light source to illuminate the first biological sample with light in the second band of excitation wavelengths and operating the fluorescence microscope according to the second in-focus setting to obtain, via the image sensor, a second image of light in the second band of emission wavelengths; and (vi) during a third period of time, using a third light source to illuminate the first biological sample with light in the third band of excitation wavelengths and operating the fluorescence microscope according to the third in-focus setting to obtain, via the image sensor, a third image of light in the third band of emission wavelengths.

In a fourth aspect, an example non-transitory computer-readable medium is disclosed. The computer readable medium has stored thereon program instructions that upon execution by a processor, cause performance of the method of the third aspect.

The features, functions, and advantages that have been discussed can be achieved independently in various examples or may be combined in yet other examples further details of which can be seen with reference to the following description and drawings.

Figure 1:
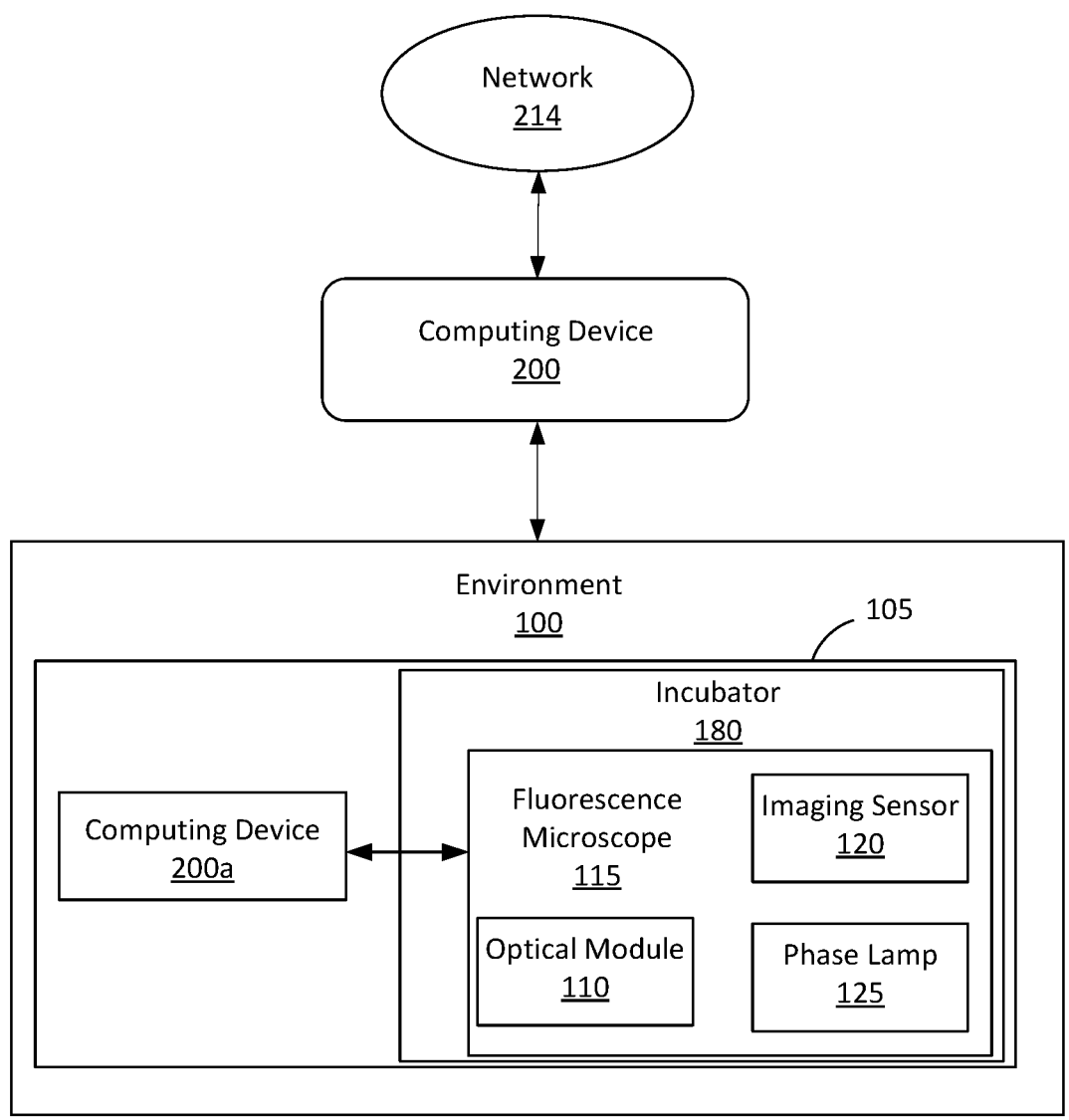
FIG. 1 is a functional block diagram of a system, according to one example implementation.

The drawings are for the purpose of illustrating examples, but it is understood that the inventions are not limited to the arrangements and instrumentalities shown in the drawings.

DETAILED DESCRIPTION

I. Overview

Microscopic imaging of live cell samples can provide information about the health, growth, and activity of populations of cells under a variety of experimental conditions. This information can include information about the number, over time, of the cells in a sample, the morphology or other structural characteristics of the cells, the internal contents or structure of the cells (e.g., contents related to a phase of mitosis or other metabolic process of the cells), or other information about the cells. This information can be used to assess the behavior of the cells under 'normal' conditions and/or under a variety of applied experimental conditions. For example, microscopic imaging of the cells could be used to assess the response of the cells to experimental pharmaceuticals or other added substances, the effects of genetic modifications of the cells, the effect on the cells of added cancerous cells, other added cell types and/or added bacteria, fungi, viruses, or other microorganisms, or the effect of some other applied experimental condition on a sample of live cells.

In order to reduce the cost of such imaging, to reduce the size of the apparatus (e.g., incubator, imaging apparatus) used to perform the imaging, to reduce the impact on the stability of conditions applied to the cell samples, and/or to provide other benefits, microscopic imaging of a plurality of live cells samples could be performed by an automated imaging apparatus configured to exist with the live cell samples inside of an incubator. Such an automated imaging apparatus could include a gantry or other actuator(s) configured to move the imaging apparatus and/or the live cell samples (e.g., a multi-well plate or other multi-sample container) to facilitate automated imaging of a plurality of live cell samples within an incubator. Such live cell samples could include a plurality of live cell samples that may differ with respect to the identity or mix of the live cell contents, the identity or amount of an added pharmaceutical, microorganism, cancer cell, or other added substance, a type of genetic modification applied to the live cell contents, or some other experimental condition.

The microscopic imaging apparatus of such a system could include mirrors, filters, or other elements to fold the optical path of the imaging apparatus so as to reduce the size of the imaging apparatus such that it can fit within the incubator. Additionally or alternatively, elements of the imaging apparatus may be separated into discrete subassemblies to facilitate various microscopic imaging modalities. For example, a phase lamp and/or other transillumination light source(s) may be provided in a module that is separate and opposite the live cell sample container from an image sensor-containing module to facilitate bright field imaging, phase contrast imaging, or other microscopic imaging modes.

Fluorescent dyes, non-fluorescent dyes or pigments, nanorods or other conductive elements that exhibit surface plasmon resonance at an appropriate wavelength, Raman dyes, or other optically distinguishable substances may be added to the live cell sample(s) to facilitate imaging the contents of the samples and/or processes or contents thereof. The optically distinguishable substance can be functionalized (e.g., with an antibody) to specifically bind to or otherwise interact with a substance of interest within the sample. For example, the contrast agent could be functionalized to specifically bind to or otherwise interact with a protein, a surface marker of a particular cell, a specific sequence of DNA/RNA/etc., or some other substance or element of interest within the biological sample. Such functionalization can facilitate imaging particular substances within the sample, e.g., imaging the presence, amount, distribution, or other information about a protein or other substance of interest in the sample. The optically distinguishable substances may be added by being introduced into the live cell samples as an extrinsic substance (e.g., by adding a specified amount of a fluorophore that is conjugated to an antibody that is specific to a particular type of cell or receptor into each well of a multi-well sample plate). Additionally or alternatively, the optically distinguishable substances may be added by genetically modifying the live cells in the samples to express the optically distinguishable substances (e.g., by adding a gene for green fluorescent protein to the live cells in the sample). Additionally or alternatively, such optically distinguishable substances may be naturally present in the live cells and/or in substances secreted thereby (e.g., autofluorescent proteins naturally expressed by a population of live cells).

Fluorophores or other substances (e.g., Raman dyes) that emit light in an emission band in response to excitation by light in an excitation band that differs from the emission band are especially useful in imaging the contents of a sample. This is due in part to the ability to distinguish the excitation light from the responsively emitted emission light, and the ability to control the magnitude and timing of the emission light by controlling the excitation light. These properties allow fluorescent dyes to be imaged with higher fidelity than other substances (e.g., dyes that scatter light within a range of wavelengths such that the wavelength of the scattered light is substantially the same as the wavelength of the illuminating light). Additionally, different fluorophores that are optically distinguishable may be used to facilitate independently imaging the multiple different fluorophores. These different fluorophores could differ with respect to excitation spectrum, emission spectrum, or other properties (e.g., fluorescence lifetime) to facilitate such independent imaging. Such imaging could be effected by providing, at respective different points in time, light at respective different excitation wavelengths of the different fluorophores. When the excitation light is delivered to the sample via the same objective lens (or objective lens system) as is used to collect and image the emission light from the sample, the process may be referred to as "epifluorescence imaging."

In order to image different fluorophores (or other optically distinguishable sample contents) at different points in time, a fluorescence imager (e.g., an epifluorescence imager) could mechanically move one or more wavelength-selective filters, mirrors, or other wavelength-selective optical elements into and out of the optical path of the imager to facilitate illumination of the sample with light in different excitation wavelength bands and/or to facilitate selective reception and imaging of light in different emission wavelength band(s). However, such an imager may be more mechanically complex, more costly, larger, less reliable, or may exhibit some other unwanted performance characteristics. Instead, the imager could include a static set of dichroic mirrors, optical filters, or other elements configured to permit different light sources to emit light in respective different excitation bands of respective different fluorophores while also permitting light in respective emission bands of the different fluorophores to be passed to, and imaged by, an image sensor.

For example, an optical module for assaying live-cell biological samples using epifluorescence capabilities in a fluorescence microscope system may include two light sources and associated filters (e.g., dichroic mirrors). The wavelengths associated with these light sources and with the pass/stop/reflect-bands of the filters within the optics module are selected to work with one or more sets of fluorophores according to the color of light they each are excited by and responsively emit at.

Such an imaging system can be configured and operated to independently excite, and to detect light responsively fluorescently emitted from, two different fluorophores that differ with respect to at least their respective excitation bands. For example, such a system could, in a first configuration, detect Green and Red fluorophores and, in a second configuration (achieved, e.g., by swapping out an optical module containing the light sources, dichroic mirrors, filters, or other optical components), detect Orange and Near Infrared ("NIR") fluorophores. Different configurations of such a two-color imaging system (e.g., different swappable optical modules of the system) could be configured to excite pairs of fluorophores that are associated with a particular assay (e.g., the fluorescence ubiquitination cell cycle indicator ("FUCCI") assay that is a genetically encoded, two-color (Red and Green) indicator that permits observation of cell division within a cell population). When the system is set in a particular configuration, independent images can only be collected for fluorophores that are compatible with the particular configuration.

Such a two-fluorophore optical system is limited with respect to the number of distinct fluorophores that it is able to independently image. Accordingly, it is limited with respect to the types of information it is able to generate in a single sample, or across a population of different samples in an automated imaging scenario (e.g., wherein different wells of a multi-well sample container differ with respect to the fluorophores present in the wells). This can include being limited with respect to the sort of fluorescent assays that can be executed in a single sample (i.e., to assays that include two or fewer fluorescent indicators). One example of such an assay is the fluorescence ubiquitination-based cell cycle indicator ("FUCCI") that is a genetically encoded, two-color (Red and Green) indicator that permits observation of cell division within a cell population. However, two-color optical modules used to perform this assay fail to differentiate between the S phase (i.e., when the cell synthesizes a complete copy of the DNA in its nucleus), the G2 phase (i.e., the second gap phase, when the cell grows more, makes proteins and organelles, and begins to reorganize its contents in preparation for mitosis) and the mitosis (M) phase (i.e., the cell separates its DNA into two sets and divides its cytoplasm, forming two new cells). There is also a colorless phase at the M/G1 transition that renders cells indistinguishable from non-expressers. TagGFP2 is a protein that possesses bright green fluorescence with excitation/emission maxima at 483 and 506 nm, respectively. During the S phase, G2 phase, and M phase, cells each emit Green fluorescence via expression of TagGFP2, which can be imaged using a two-color optical module. mKate is a far-red fluorescent protein that possesses fluorescence with excitation/emission maxima at 588 and 633 nm, respectively. During the G1 phase (i.e., first gap phase, when the cell grows physically larger, copies organelles, and makes molecular building blocks for later stages of growth) and transition into S phase, cells emit far-red fluorescence via expression of mKate, which can be also be imaged using the two-color optical module. However, such a two-color optical module would not be able to use additional fluorescent indicators to identify additional phases or sub-phases within the cell division process.

The capability of such a two-fluorophore imaging system could be expanded by swapping out an optical module that includes the light sources, filters, mirrors, or other optical elements related to the excitation and emission bands of the two fluorophores. However, such manual swapping may be difficult to perform while an automated imaging experiment is being done and would require the environment of the live cell samples to be severely perturbed by opening the incubator such that the module can be swapped.

It is beneficial in a variety of applications to be able to use a fluorescent imaging apparatus to independently image three (or more) fluorescent channels (without swapping an optical module or performing some other manual process that may result in perturbation of the incubation environment). Such a system could allow for more the use of more complex assays (e.g., assays that include three or more fluorescent indicators like a three-color FUCCI assay observing a complete cell cycle), the identification of more types of cells in a single sample while also assessing metabolic or other fluorescent indicators (e.g., two or more fluorescent indicators to tag respective different cells types, while a third fluorescent indicator in the sample represents metabolism, dell death, or some other process of interest), the use of more types of assays/individual fluorescent indicators in an individual sample in an incubator and/or more types of assays/individual fluorescent indicators in different samples in an incubator. These benefits could reduce costs by reducing the time and incubator space needed to perform a specified number of experiments/assays by allowing multiplexing of multiple different assays of a single experiment in a single sample and/or by allowing different assays of different experiments to be performed in different wells of a sample plate in a single incubator.

The embodiments herein provide methods and systems relating to such a three (or more) channel microscopic fluorescent imaging process in a manner that is compatible with automated multi-sample imaging within an incubator. These embodiments provide solutions to the increased complexity that comes with fitting a three (or more) channel fluorescent imaging apparatus into a limited volume/dimension while also permitting that imaging apparatus to also be used to bright field and/or phase contrast microscopy. These embodiments also provide solutions to the complicated problem of specifying a branching optical path that routes excitation light in three (or more) excitation bands to a sample while also routing light from the sample in three (or more) emission bands to an image sensor while also rejecting light in the excitation bands. Some of these embodiments include providing a phase lamp (or other transillumination light source) that is part of a removable module that is paired with a corresponding three (or more) channel fluorescent imaging module. Such a pairing may be necessary to ensure that light from the phase lamp includes wavelengths that are able to pass through the paired fluorescent imaging module. Such an illumination module and paired optical filter module could include barcodes, onboard memory, or other features to facilitate automated module detection and identification so as to warn users, prior to running an experiment, if the modules are mis-matched.

Embodiments provided herein also include improvements to the apparatus used to manually swap optical modules (e.g. phase lamp modules, light source and filter modules) that improve the seating and alignment of such modules within an imaging apparatus and that increase the ease with which users can perform such manual swapping. In prior systems, a separate tool was needed to couple and decouple the various optical modules from the system. The tool was difficult to align with a corresponding screw through a small hole in the optical module. In addition, the force required to couple or decouple the optical module was difficult for many end users to generate, in part due to the arrangement and configuration of the electrical connector used to electrically couple the light sources within the module to controllers and power sources of the rest of the system. As a result, many end users required assistance to swap the optical modules.

The flexible interchangeability of the optical modules enables the system to be configured to permit different combinations of methods for detecting fluorophores including, but not limited to: (i) activating three light sources in three different bands of excitation wavelengths to direct excitation light to a sample, and detecting responsively emitted emission light from three distinct fluorophores (e.g., Green, Orange, and near infrared ("NIR")), (ii) activating three light sources in three different bands of excitation wavelengths, with two of the excitation wavelengths directed to a Forster resonance energy transfer ("FRET")-based measurement (e.g., ATP) and the third band of excitation wavelengths to identify an independent fluorophore (e.g., a nuclear label), and (iii) using only two light sources of an optical module in two different bands of excitation wavelengths, and detecting responsively emitted emission light from two distinct fluorophores (e.g., (a) Green and Red or (b) Orange and NIR).

In addition, a phase lamp matched to the filters in the three (or more) band optical module may also be included in the system to advantageously permit phase and bright-field imaging to be performed (e.g., in order to augment fluorescent imaging information and/or to provide independent image information, to further process and refine images to identify fluorophores, to measure FRET, or to provide some other benefit). One advantage of the phase lamp modules (or other transillumination light source modules) of the present disclosure is the ability of the system to directly identify that a specific phase lamp module that has been installed. Detecting the identity of the phase lamp beneficially permits the system to determine when there is an invalid configuration in which the phase lamp is not the correct match for the given optical module (which can result, e.g., in the light from the phase lamp being wholly or partially blocked from being transmitted through the optical module to be imaged) and to alert a user before experiments (e.g., experiments that include performing one or more assays) are run.

II. Example Architecture

FIG. 1 is a block diagram showing an operating environment 100 that includes or involves, for example, a system 105 for assaying live-cell biological samples that includes a fluorescence microscope 115 in electrical communication with a computing device 200a. The fluorescence microscope 115 is located within an incubator 108 that is configured to control a temperature, humidity, and/or other environmental parameters to facilitate culturing of live cell samples that can be imaged, in automated fashion, by the fluorescence microscope 115. By being positioned within the incubator 180, the fluorescence microscope 115 can image the samples without requiring the samples to be removed from the incubator 180, a process which could perturb the samples and modify their growth/response to applied experimental conditions. Method 300 in FIG. 16 described below shows an implementation of a method that can be implemented within this operating environment 100.

The fluorescence microscope 115 includes an optical module 110 that can be used, in combination with the imaging sensor 120, to image samples in the incubator 180 using epifluorescence imaging. The optical module 110 includes three (or more) light sources configured to provide illumination in three (or more) respective bands of excitation wavelengths that correspond to respective fluorophores in the sample (e.g., fluorescent indicators that include a fluorophore conjugated to an antibody or other structure to facilitate selectively binding to a protein or other substance of interest). The optical module 110 additionally includes dichroic mirrors, filters, and/or other elements configured to provide a branched optical path such that light from the three (or more) light sources is delivered, via an objective, to the sample. The objective may be a part of the optical module 110 or may be separate from it. The optical module 110 is also configured to deliver responsively emitted fluorescent light, in three (or more) respective bands of emission wavelengths, that has been collected through the objective to the imaging sensor 120 to facilitate epifluorescent imaging of the three different fluorophores in the sample.

Being able to independently epifluorescently image three different fluorophores using a single optical module 110 provides a variety of benefits. It can facilitate using more complex three (or more) color assays. It can facilitate imaging multiple assays or other fluorescent indicators in a single sample (e.g., a two-color FUCCI assay and an independent fluorescent indicator that selectively binds to cells of a particular type, allowing both the identity and cell division phase of cells in the sample to be determined). It can facilitate fluorophore/assay selection by relaxing the requirement that all indicators/assays conform to only two sets of excitation/emission bands (e.g., a more optimal fluorescent indicator can be selected for a particular use instead of selecting a less-optimal indicator that matches one of the two available excitation/emission bands of a two-color optical module). It can facilitate imaging different sets of assays/fluorescent indicators in different samples contained in the same incubator to save time and other costs by allowing the space within a single instrument/incubator to be more efficiently used. For example, first and second different experiments, having respective first and second sets of fluorescent indicators/assays (that may overlap with respect to emission/excitation wavelengths), could be run in respective sets of wells in the same incubator. Additionally or alternatively, a single experiment could be run with multiple different sets of assays/fluorescent indicators present in sub-sets of the wells used to perform the single experiment, allowing additional data about the experiment to be generated using the same incubator at the same time. Being able to independently epifluorescently image three (or more) different fluorophores using a single optical module 110 could provide additional or alternative benefits or combinations of benefits.

The fluorescence microscope 115 also includes a phase lamp 125 (or other transillumination light source) configured to provide light for phase contrast, bright field, or other forms of imaging. The optical module 110 is configured to pass at least some of the light emitted from the phase lamp 125. In some examples, this could include the phase lamp 125 being a narrow-band light source (e.g., a laser, an LED) and the optical module being configured to pass light across the narrow band of wavelengths emitted by the narrow-band light source. Details of the optical module 110 and phase lamp 125 are provided elsewhere herein (e.g., in relation to FIGS. 3-15).

The optical module 110 can be made user-swappable (e.g., according to the embodiments described elsewhere herein) in order to use the fluorescence microscope 115 to image different fluorescent indicators/assays during different periods of time. This could include the optical module having pins, slots, or other alignment features to facilitate aligning the optical module 110 with other imaging components of the fluorescence microscope 115 (e.g., with the imaging sensor 120). This can also include the optical module 110 having one or more electrical connectors to facilitate powering and controlling three (or more) light sources or providing some other functionality. For example, the optical module 110 could include a memory or other electrical components to allow a computing device (e.g., 200, 200a) to identify the optical module 110 and/or to determine the bands of wavelengths of light that can be emitted from and/or imaged using the optical module 110.

The phase lamp 125 (or other transillumination light source) could also be made user-swappable. This could be due to different swappable optical modules 110 having different pass-bands (i.e., bands in which wavelengths of light from a sample that can be passed through the optical module 110 to the imaging sensor 120) that may not be compatible with every possible phase lamp 125. For example, a first phase lamp 125 may be 'optimal' in some sense (e.g., with respect to phase contrast imaging a particular type of sample), but could produce light in a band of wavelengths that does not significantly overlap with any pass-band of an optical module 110 that has been selected to perform an experiment (e.g., to facilitate imaging a particular assay of interest). Accordingly, the first phase lamp 125 module could be swapped with a second phase lamp 125 module that emits light at wavelength(s) wholly or substantially within the passband(s) of the selected optical module 110.

Such swappable phase lamp 125 modules could include memory or other electrical components to allow a computing device (e.g., 200, 200a) to identify the phase lamp 125 module and/or to determine the bands of wavelengths of light that can be emitted from the phase lamp 125 module. This identity/information could be automatically compared to similar information/identity of the optical module 110 installed in the fluorescence microscope 115 to ensure that the installed modules are compatible (e.g., to ensure that the installed optical module 110 can pass wavelengths of light emitted from the installed phase lamp 125 module, so that the combination can be used to image samples via phase contrast, bright field, or some other imaging modality using the phase lamp 125 module). If an incompatibility is detected, a user could be warned prior to initiating an automated imaging trial or other experiment using the system 105.

Figure 2:
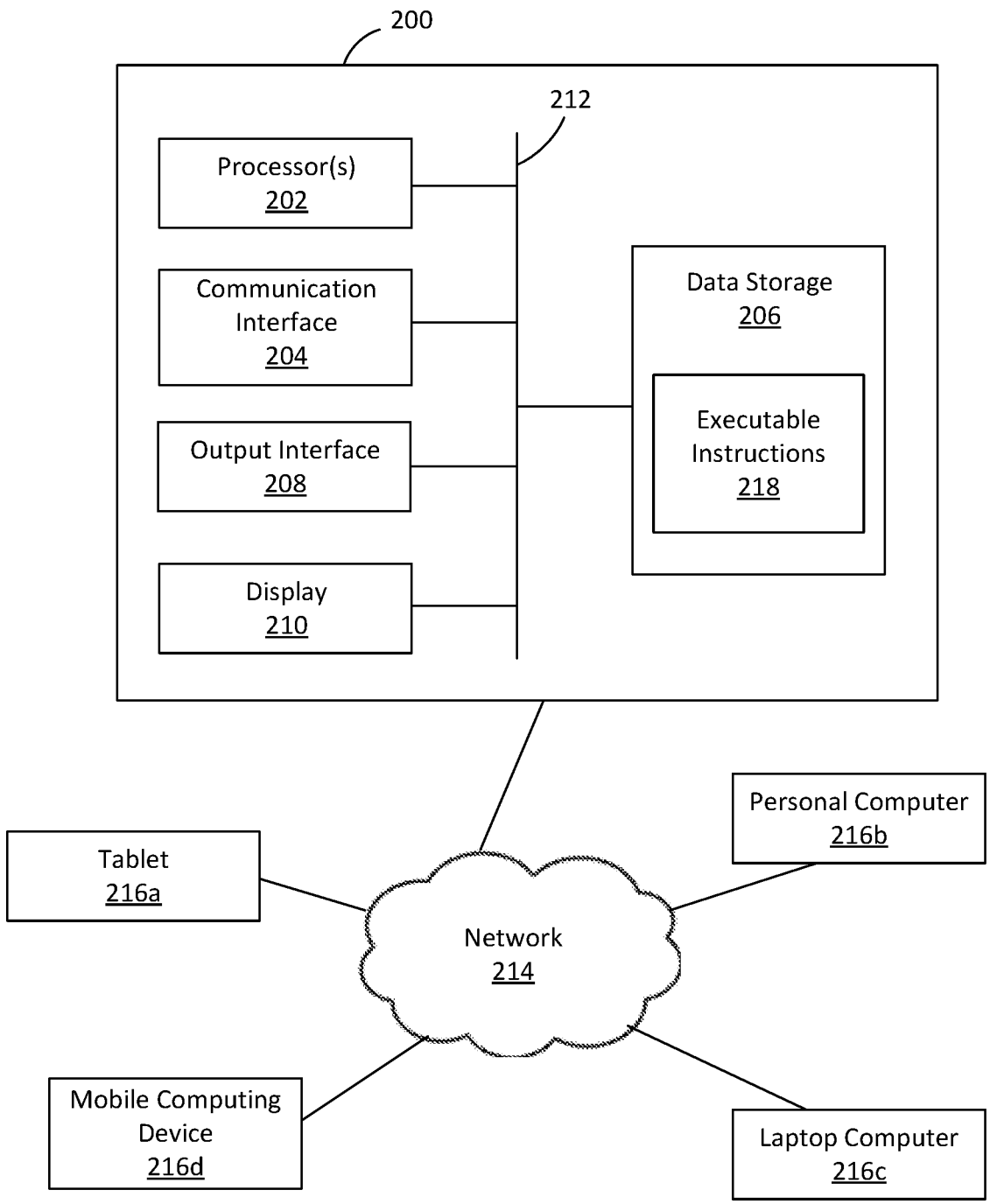
FIG. 2 depicts a block diagram of a computing device and a computer network, according to an example implementation.

FIG. 2 is a block diagram illustrating an example of a computing device 200, according to an example implementation, that is configured to interface with operating environment 100, either directly or indirectly. The computing device 200 may be used to perform functions of the method shown in FIG. 16 and described below. In particular, computing device 200 can be configured to perform one or more functions, including, but not limited to, using a single optical module to obtain images of three or more fluorescence colors in a single biological sample in a single vessel or in multiple vessels. The obtained images may then be used to perform additional analyses about the imaged biological sample(s) related to the properties of the fluorophores and/or substances conjugated thereto that correspond to the three or more fluorescence colors. The functions may also include using light sources not a part of the single optical module (e.g., a phase lamp) to obtain bright field images, phase contrast images, or some other images of a sample using the signal optical module and the other light source(s).

The availability of three or more colors imaged in a single sample facilitates more complicated multi-color analyses or assays (e.g., a three-color FUCCI assay observing a complete cell cycle), the performance of multiple different assays in a single sample or in different samples (e.g., a two-color FUCCI assay (Green/Orange) in conjunction with Annexin NIR assay for cell apoptosis), the use of one or more fluorescent indicators in combination with each other and/or with one or more multi-color assays (e.g., two fluorescent reporters to identify respective cell types and an Annexin NIR assay for cell apoptosis which may be used as part of a three-color immune cell killing assay), the use of different sets of indicators/assays in different samples located in the same incubator, or other examples. The availability of three or more colors can also relax the requirements for selected indicators/assays, allowing for more flexibility. For example, if a particular assay is only available in a particular color, that color could be reserved for the assay while the other colors could be used for cell-type-specific indicators or other applications (e.g., color channels of an assay for which more color options are available).

The computing device 200 has a processor(s) 202, and also a communication interface 204, data storage 206, an output interface 208, and a display 210 each connected to a communication bus 212. The computing device 200 may also include hardware to enable communication within the computing device 200 and between the computing device 200 and other devices (e.g. not shown). The hardware may include transmitters, receivers, and antennas, for example.

The communication interface 204 may be a wireless interface and/or one or more wired interfaces that allow for both short-range communication and long-range communication to one or more networks 214 or to one or more remote computing devices 216 (e.g., a tablet 216a, a personal computer 216b, a laptop computer 216c and a mobile computing device 216d, for example). Such wireless interfaces may provide for communication under one or more wireless communication protocols, such as Bluetooth, Wi-Fi (e.g., an institute of electrical and electronic engineers (IEEE) 802.11 protocol), Long-Term Evolution (LTE), cellular communications, near-field communication (NFC), and/or other wireless communication protocols. Such wired interfaces may include Ethernet interface, a Universal Serial Bus (USB) interface, or similar interface to communicate via a wire, a twisted pair of wires, a coaxial cable, an optical link, a fiber-optic link, or other physical connection to a wired network. Thus, the communication interface 204 may be configured to receive input data from one or more devices, and may also be configured to send output data to other devices.

The communication interface 204 may also include a user-input device, such as a keyboard, a keypad, a touch screen, a touch pad, a computer mouse, a track ball and/or other similar devices, for example.

The data storage 206 may include or take the form of one or more computer-readable storage media that can be read or accessed by the processor(s) 202. The computer-readable storage media can include volatile and/or non-volatile storage components, such as optical, magnetic, organic or other memory or disc storage, which can be integrated in whole or in part with the processor(s) 202. The data storage 206 is considered non-transitory computer readable media. In some examples, the data storage 206 can be implemented using a single physical device (e.g., one optical, magnetic, organic or other memory or disc storage unit), while in other examples, the data storage 206 can be implemented using two or more physical devices.

The data storage 206 thus is a non-transitory computer readable storage medium, and executable instructions 218 are stored thereon. The instructions 218 include computer executable code. When the instructions 218 are executed by the processor(s) 202, the processor(s) 202 are caused to perform functions. Such functions include, but are not limited to, using a single optical module to obtain images of three or more fluorescence colors in a single biological sample in a single vessel or in multiple vessels, to use a phase lamp or other light source in addition to the single optical module to obtain bright field images, phase contrast images, or some other images of the biological sample in combination with the single optical module, and/or to perform analyses based on the obtained images.

The processor(s) 202 may be a general-purpose processor or a special purpose processor (e.g., digital signal processors, application specific integrated circuits, etc.). The processor(s) 202 may receive inputs from the communication interface 204, and process the inputs to generate outputs that are stored in the data storage 206 and output to the display 210. The processor(s) 202 can be configured to execute the executable instructions 218 (e.g., computer-readable program instructions) that are stored in the data storage 206 and are executable to provide the functionality of the computing device 200 described herein.

The output interface 208 outputs information to the display 210 or to other components as well. Thus, the output interface 208 may be similar to the communication interface 204 and can be a wireless interface (e.g., transmitter) or a wired interface as well. The output interface 208 may send commands to one or more controllable devices, for example.

The computing device 200 shown in FIG. 2 may also be representative of a local computing device 200a (FIG. 1) in operating environment 100, for example, in communication with the system 105. This local computing device 200a may perform one or more of the steps of the method 300 described below, may receive input from a user and/or may send image data and user input to computing device 200 to perform all or some of the steps of method 300.

Figure 16:
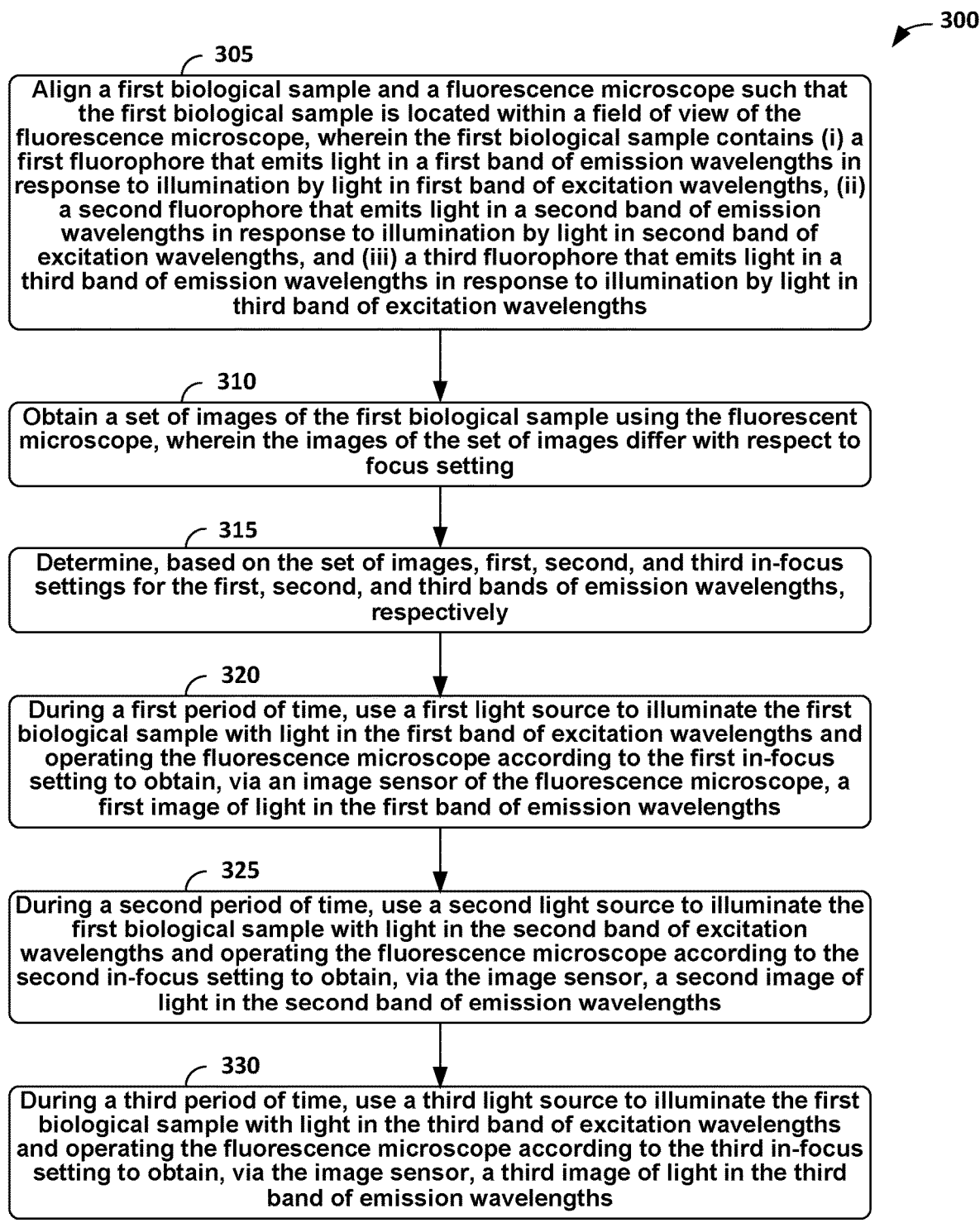
FIG. 16 shows a flowchart of a method, according to an example implementation.

FIG. 16 shows a flowchart of an example method 300 to image fluorophores in live-cell biological samples. The method 300 includes aligning a first biological sample and a fluorescence microscope such that the first biological sample is located within a field of view of the fluorescence microscope, wherein the first biological sample contains (i) a first fluorophore that emits light in a first band of emission wavelengths in response to illumination by light in first band of excitation wavelengths, (ii) a second fluorophore that emits light in a second band of emission wavelengths in response to illumination by light in second band of excitation wavelengths, and (iii) a third fluorophore that emits light in a third band of emission wavelengths in response to illumination by light in third band of excitation wavelengths (305); obtaining a set of images of the first biological sample using the fluorescent microscope, wherein the images of the set of images differ with respect to focus setting (310); determining, based on the set of images, first, second, and third in-focus settings for the first, second, and third bands of emission wavelengths, respectively (315); during a first period of time, using a first light source to illuminate the first biological sample with light in the first band of excitation wavelengths and operating the fluorescence microscope according to the first in-focus setting to obtain, via an image sensor of the fluorescence microscope, a first image of light in the first band of emission wavelengths (320); during a second period of time, using a second light source to illuminate the first biological sample with light in the second band of excitation wavelengths and operating the fluorescence microscope according to the second in-focus setting to obtain, via the image sensor, a second image of light in the second band of emission wavelengths (325); during a third period of time, using a third light source to illuminate the first biological sample with light in the third band of excitation wavelengths and operating the fluorescence microscope according to the third in-focus setting to obtain, via the image sensor, a third image of light in the third band of emission wavelengths (330). Method 300 shown in FIG. 16 presents an example of a method that could be used with the computing device 200 of FIG. 2, for example. In some instances, components of the systems may be configured to perform the functions such that the components are configured and structured with hardware and/or software to enable such performance. Components of the systems may be arranged to be adapted to, capable of, or suited for performing the functions, such as when operated in a specific manner. Method 300 may include one or more operations, functions, or actions as illustrated by one or more of blocks 305-330. Although the blocks are illustrated in a sequential order, some of these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of the present examples. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time such as register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIG. 16, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

III. Example Optical Module

Figure 3:
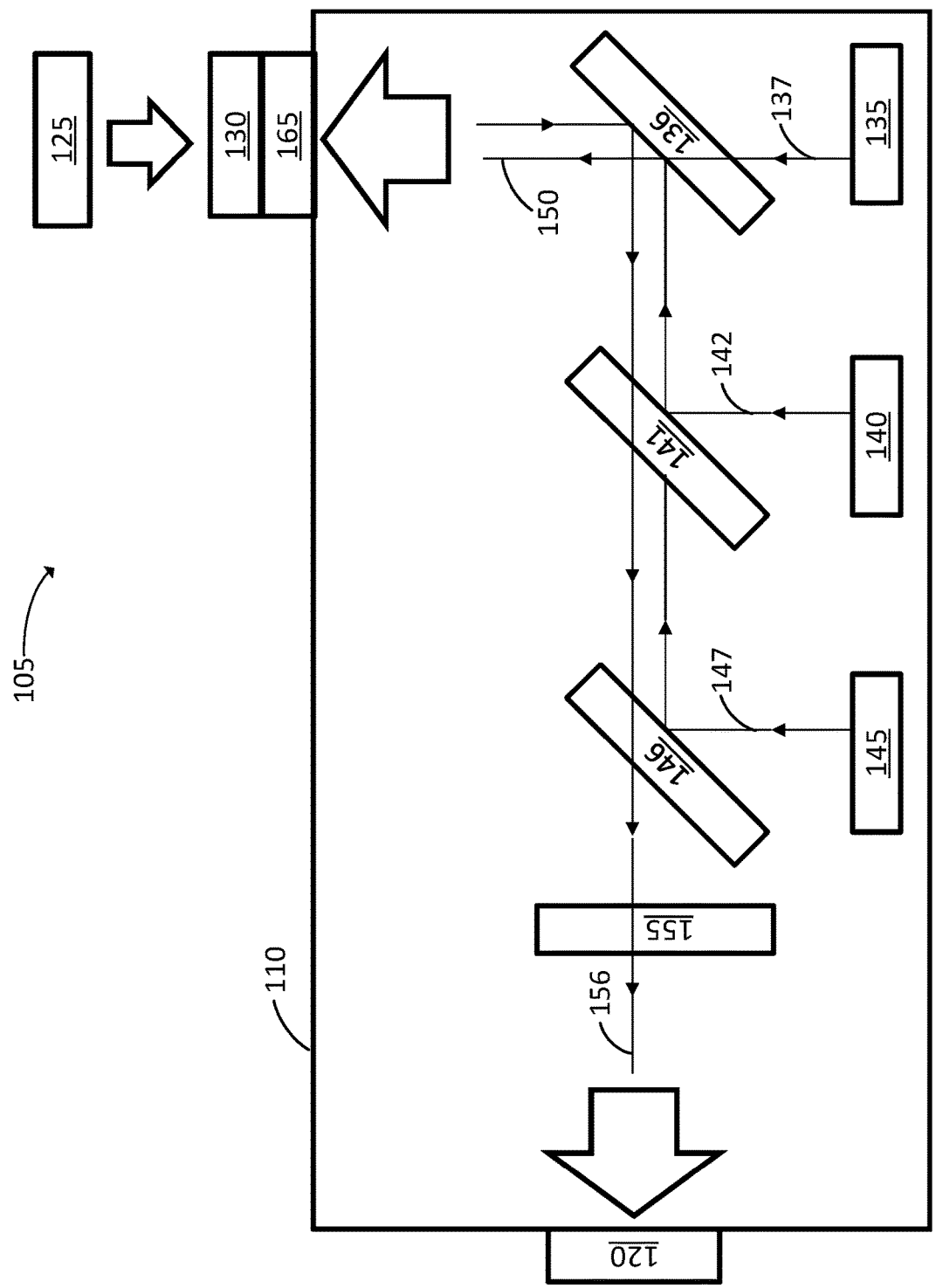
FIG. 3 shows a functional block diagram of a system for assaying live-cell biological samples, including an optical module, according to an example implementation.
Figure 4:
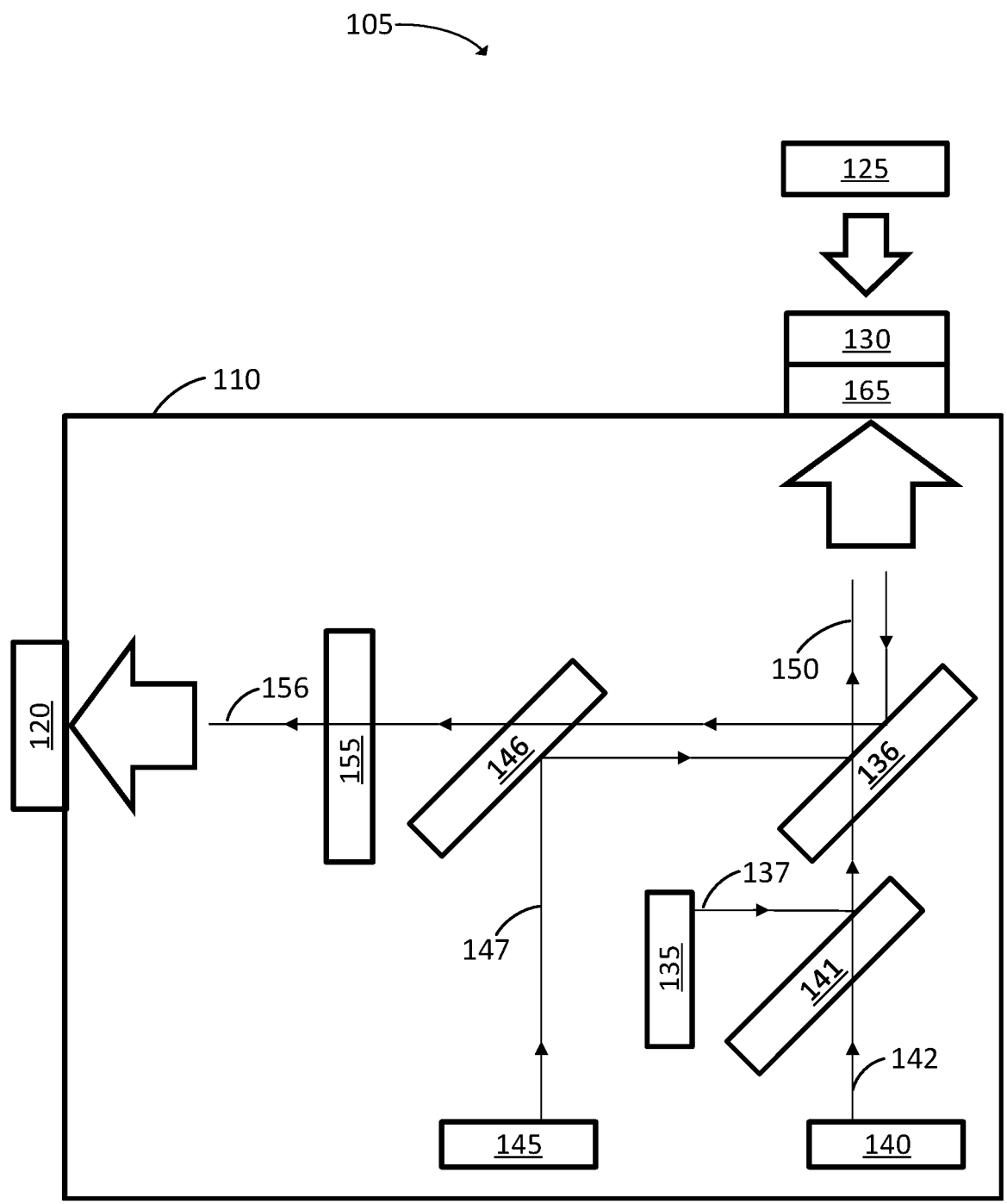
FIG. 4 shows a functional block diagram of a system for assaying live-cell biological samples, including an optical module, according to an example implementation.
Figure 5:
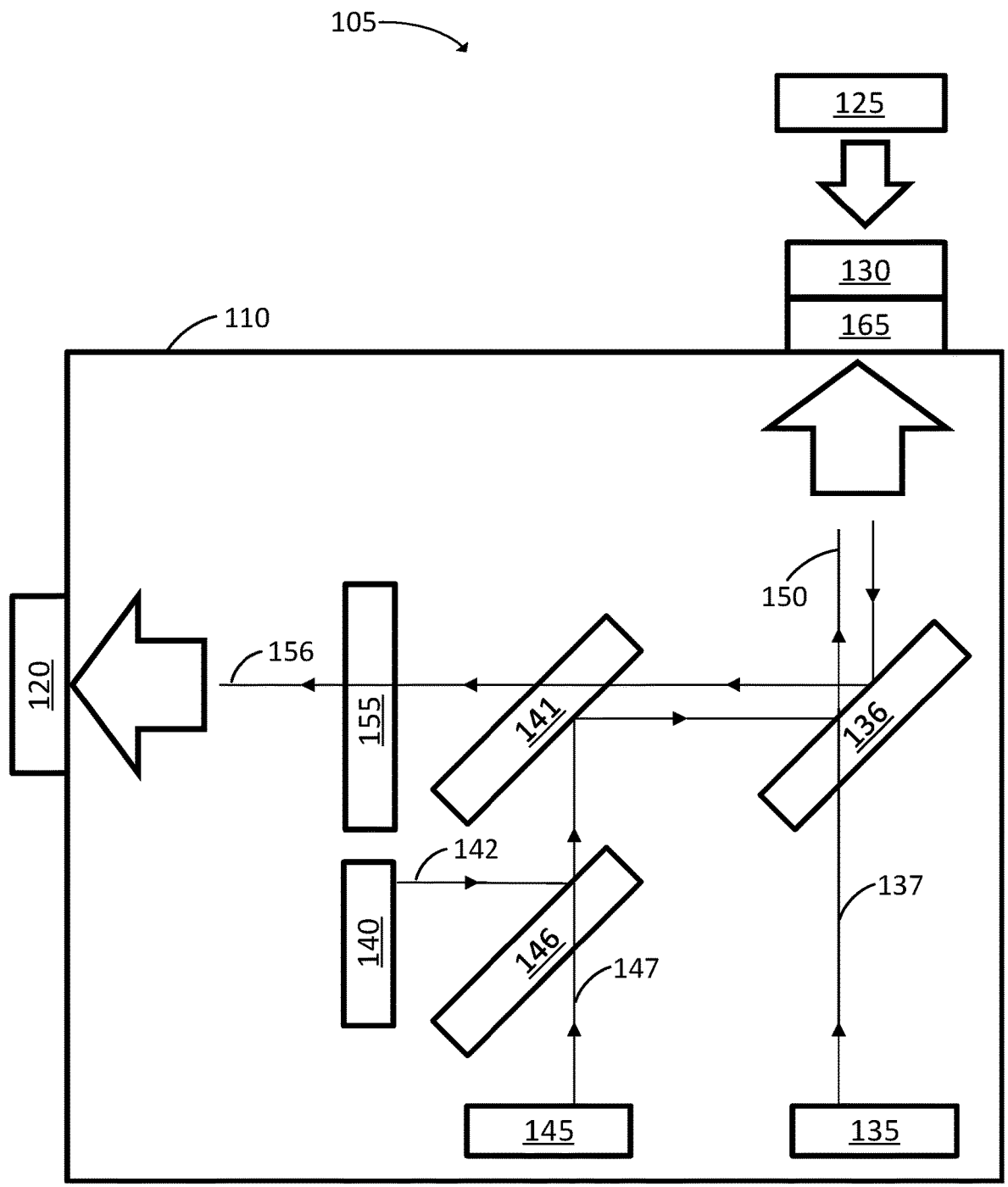
FIG. 5 shows a functional block diagram of a system for assaying live-cell biological samples, including an optical module, according to an example implementation.
Figure 6:
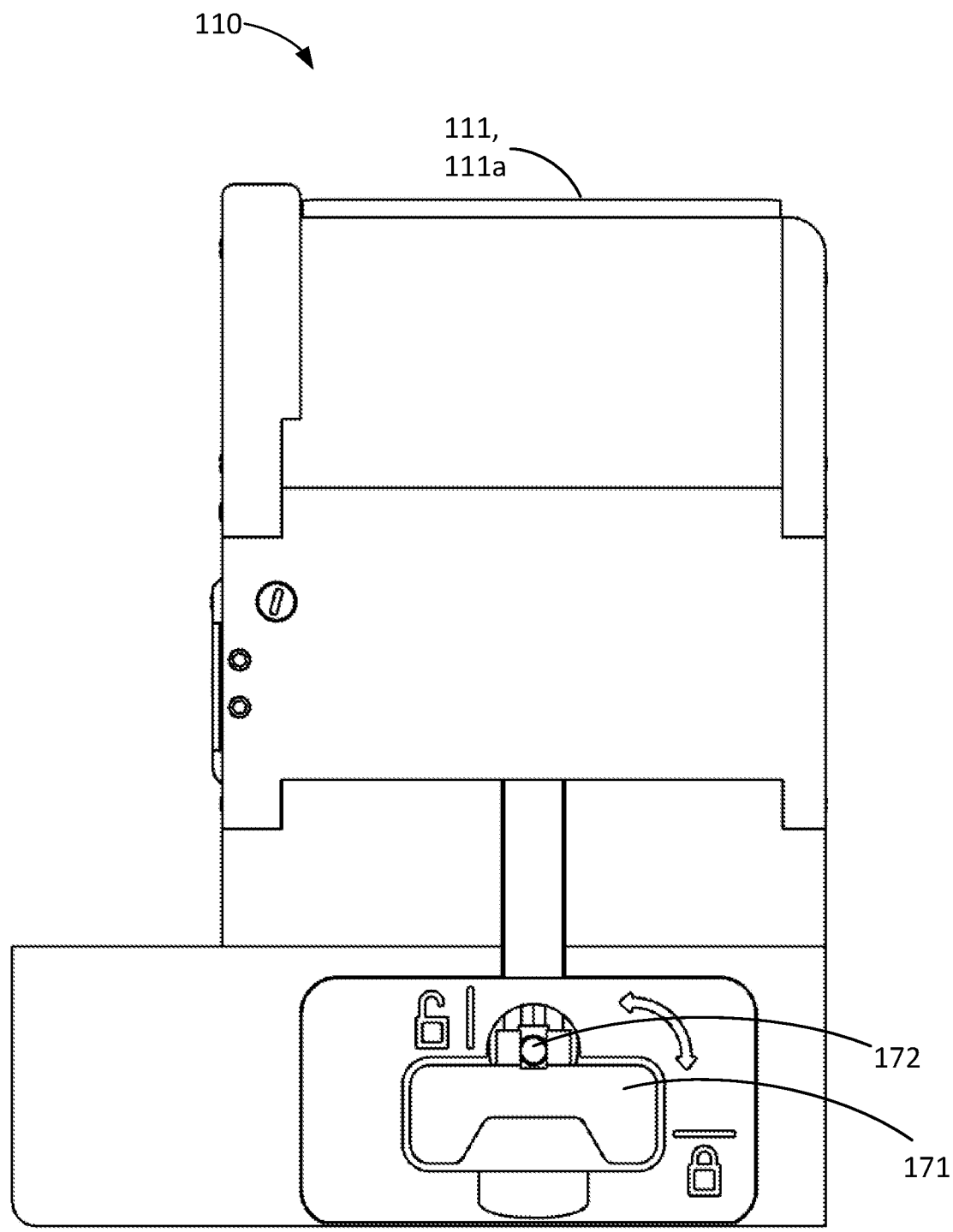
FIG. 6 shows a front view of the optical module, according to an example implementation.
Figure 7:
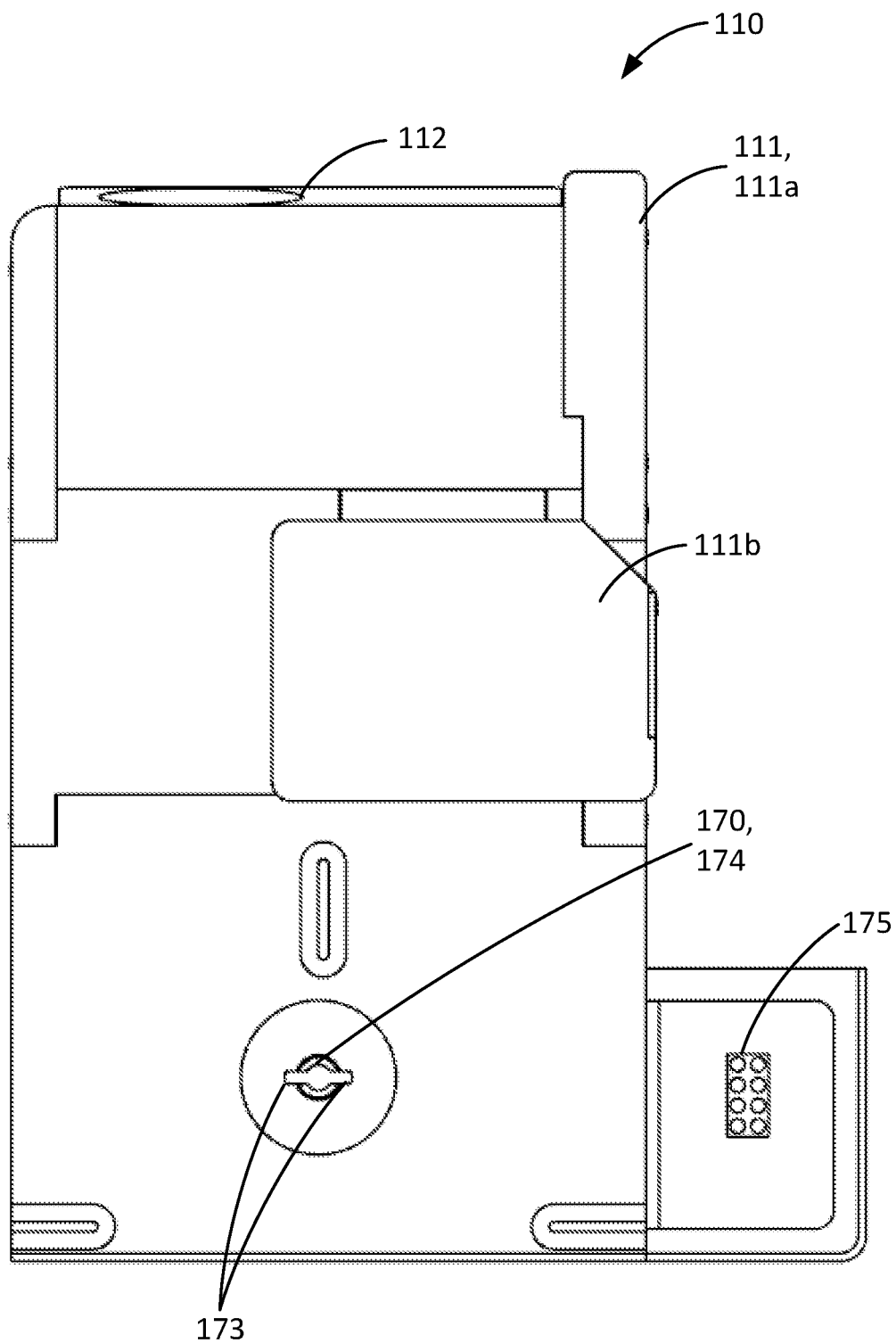
FIG. 7 shows a rear view of the optical module, according to the example implementation of FIG. 6.
Figure 8:
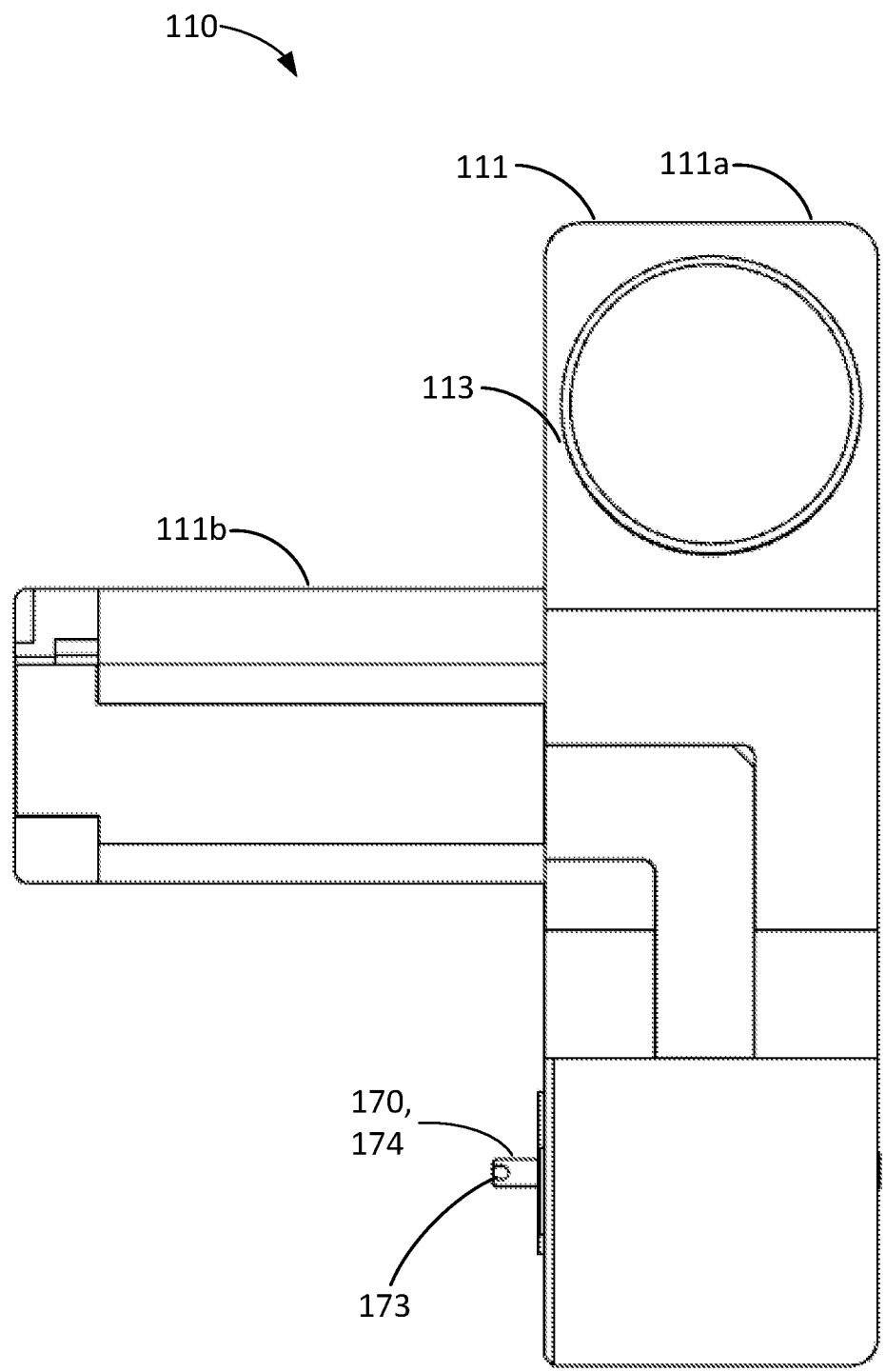
FIG. 8 shows a side view of the optical module, according to the example implementation of FIG. 6.
Figure 9:
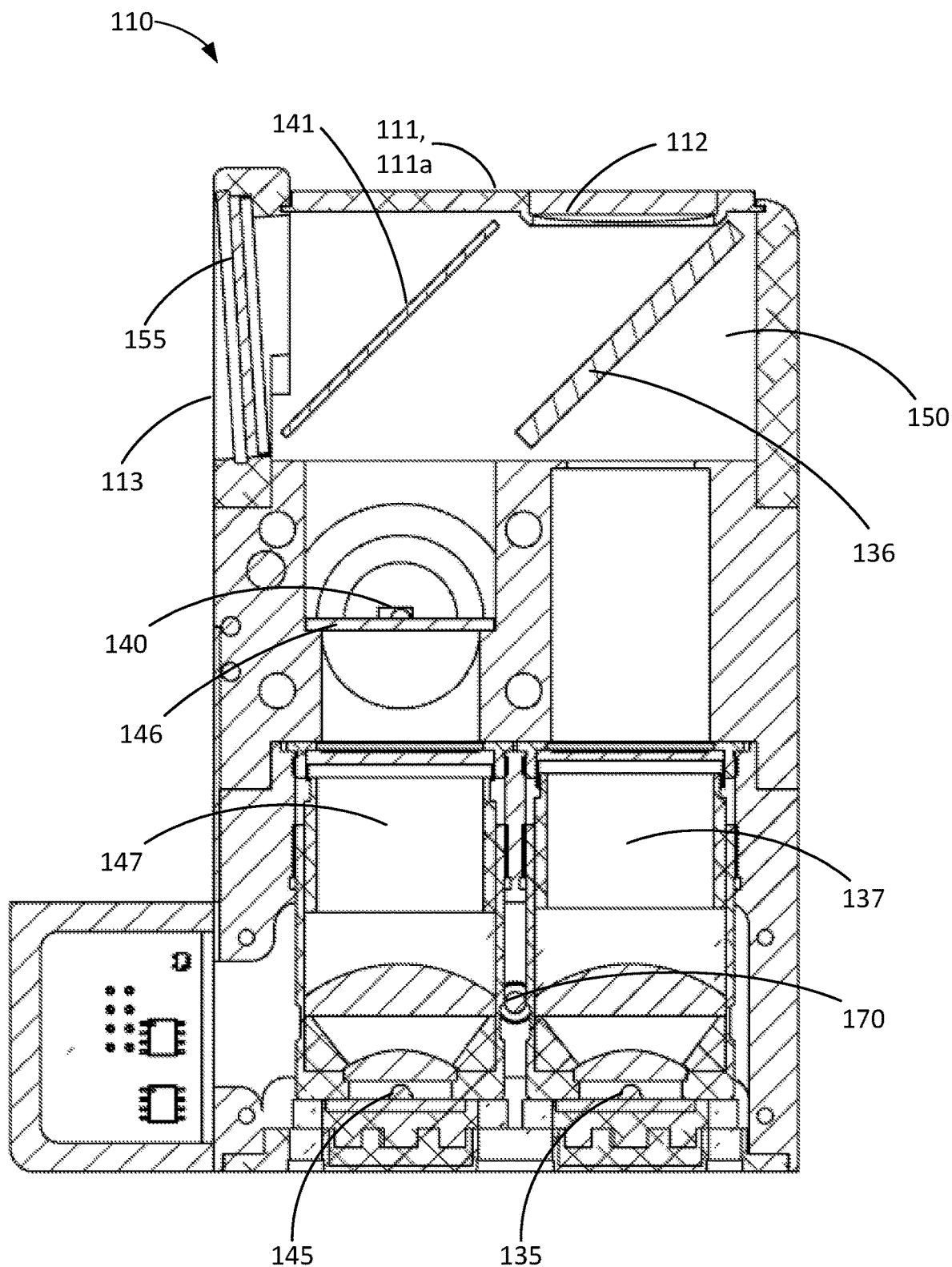
FIG. 9 shows a front cross-sectional view of the optical module, according to the example implementation of FIG. 6.
Figure 10:
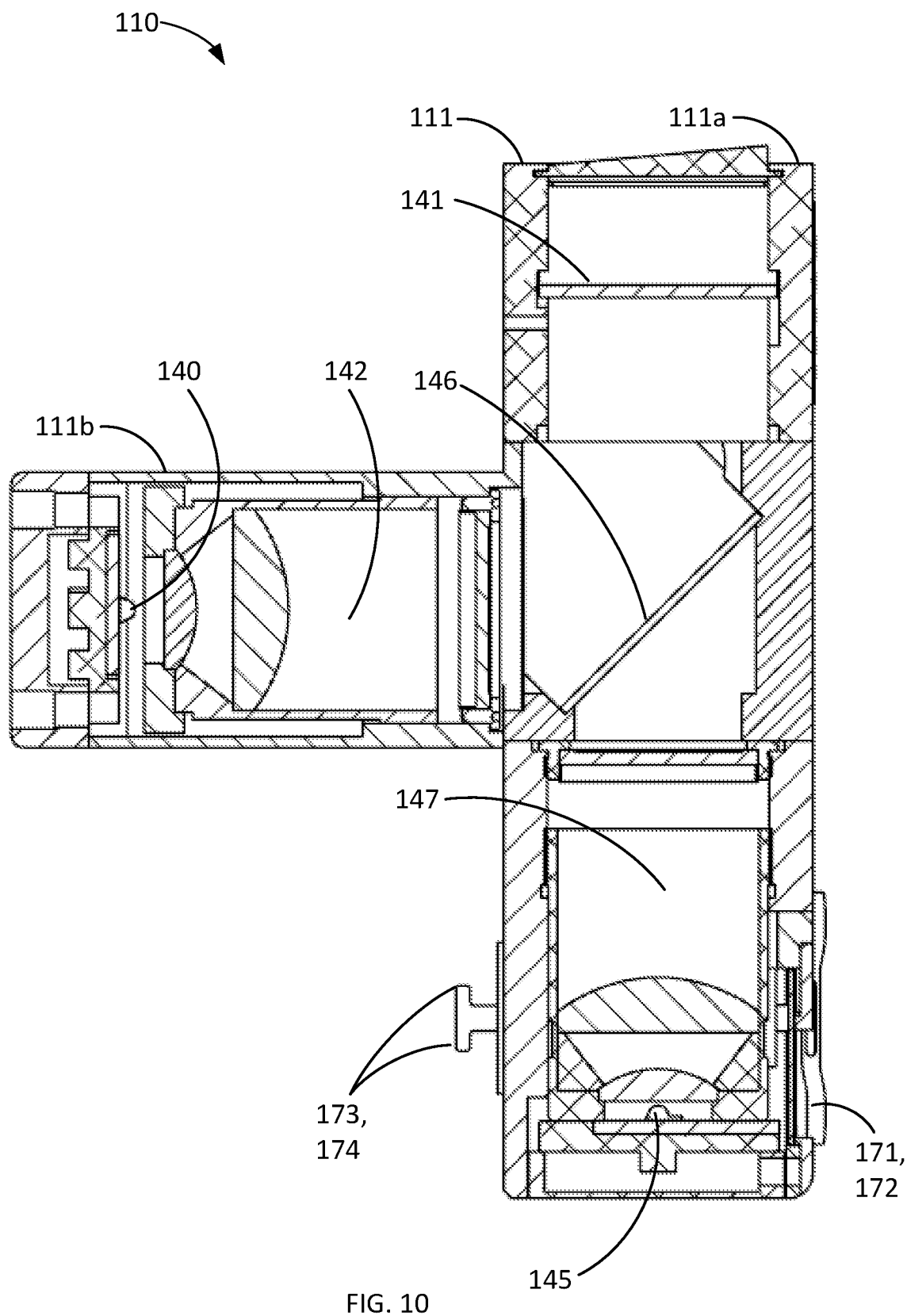
FIG. 10 shows a side cross-sectional view of the optical module, according to the example implementation of FIG. 6.
Figure 11:
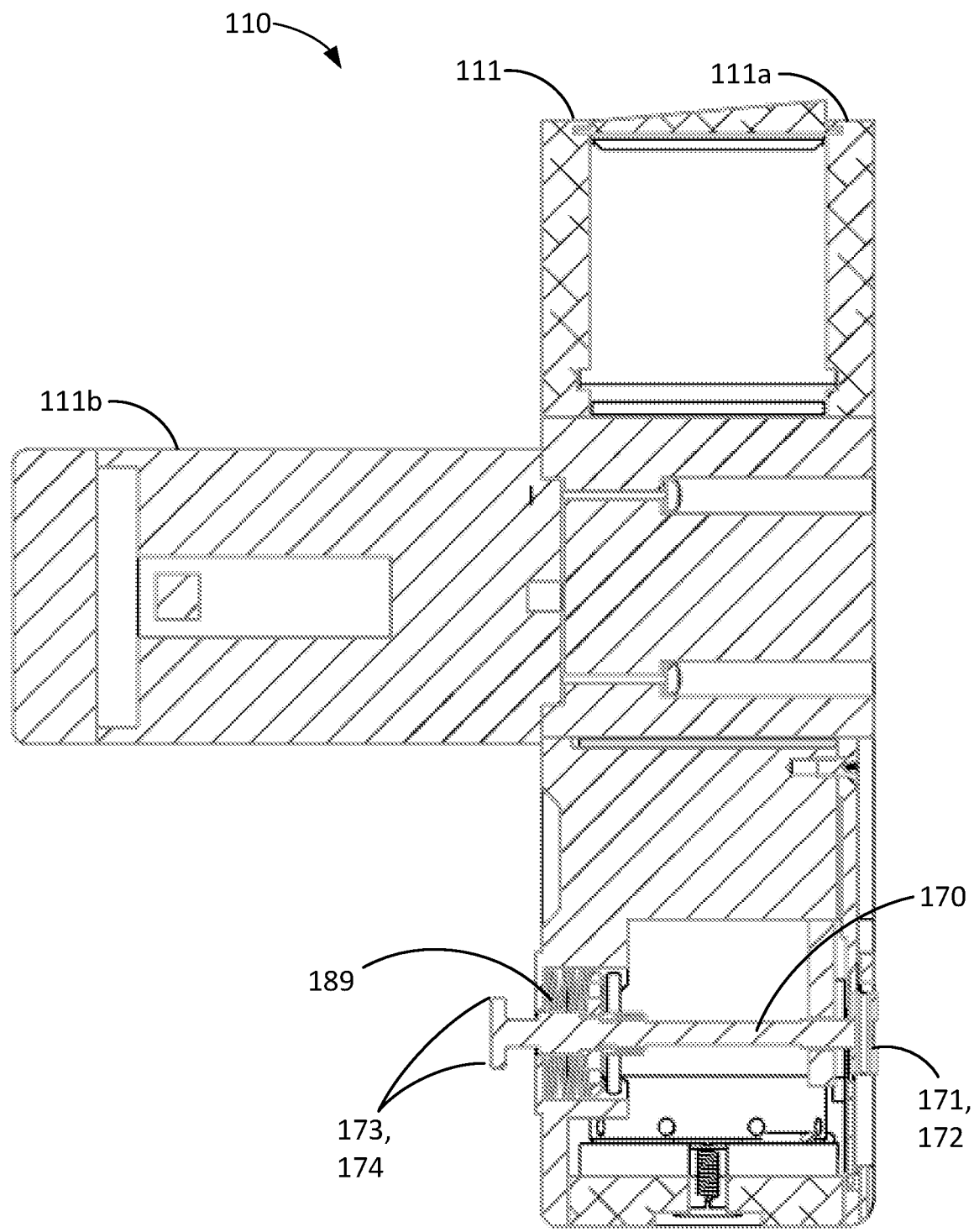
FIG. 11 shows a side cross-sectional view of the optical module, according to the example implementation of FIG. 6.
Figure 12:
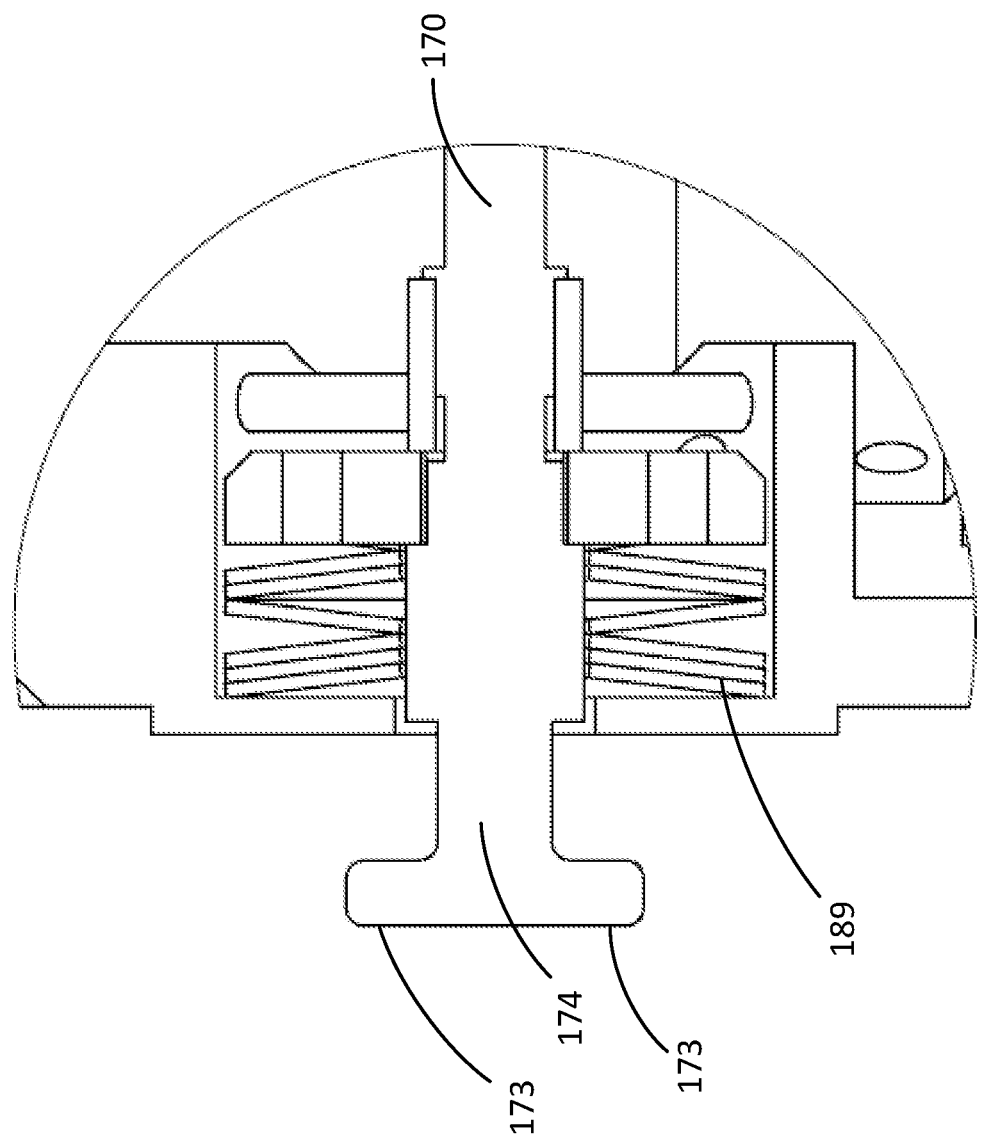
FIG. 12 shows a detail view of the shaft of the optical module, according to the example implementation of FIG. 11.
Figure 13:
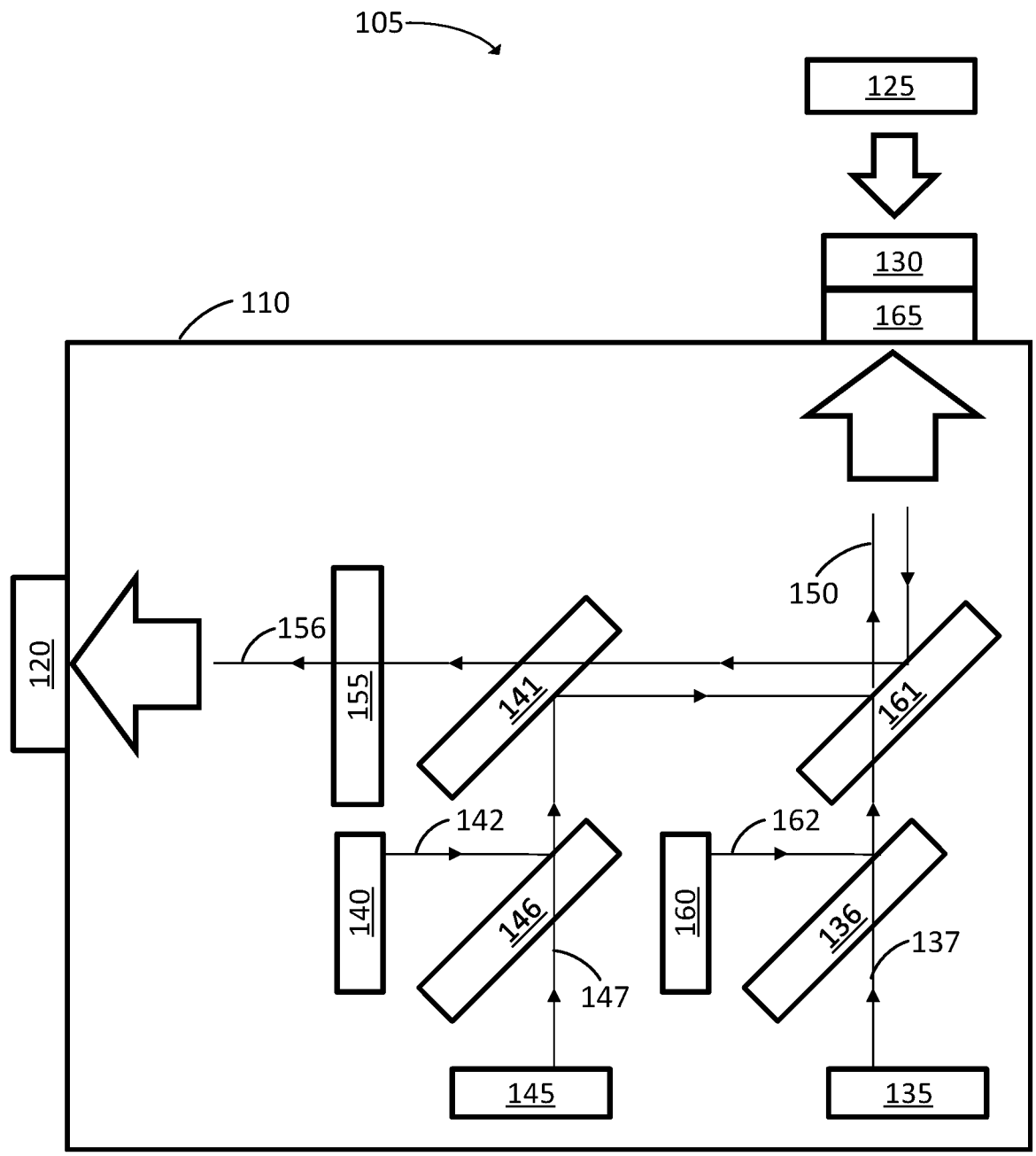
FIG. 13 shows a functional block diagram of a system for assaying live-cell biological samples, including an optical module, according to an example implementation.
Figure 14:
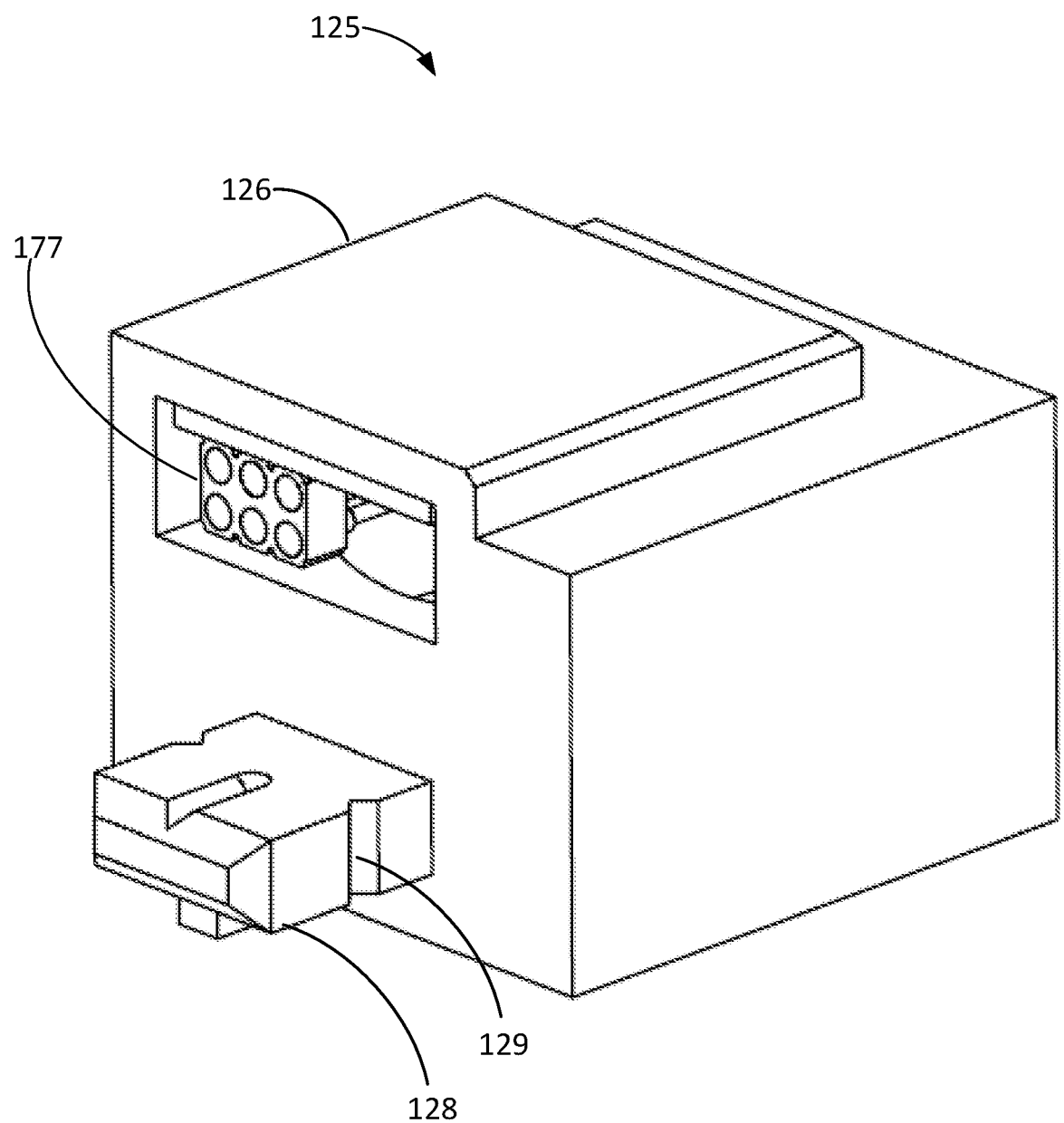
FIG. 14 shows a perspective view of a phase lamp, according to an example implementation.
Figure 15:
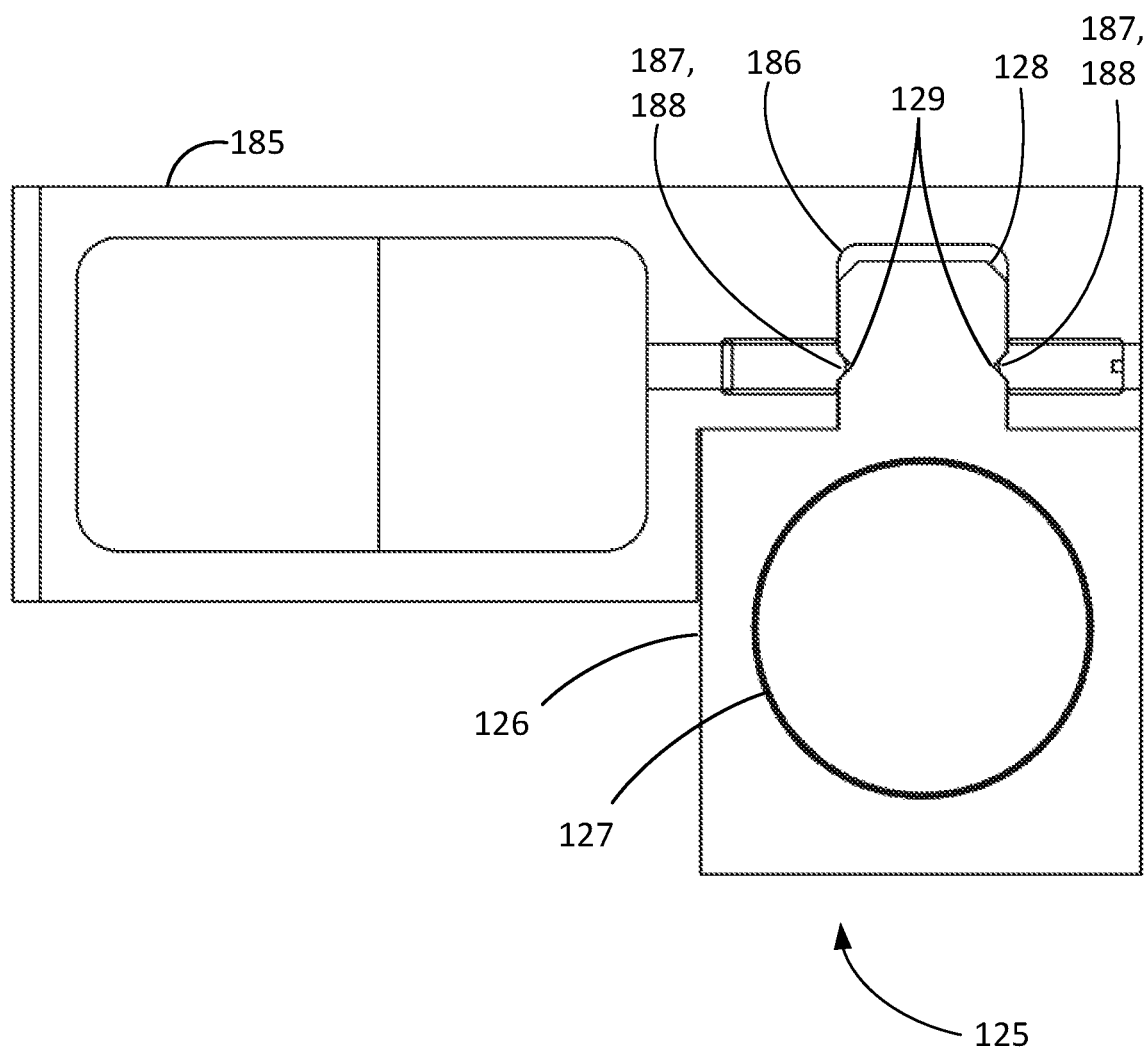
FIG. 15 shows a section view of a phase lamp coupled to a fluorescence microscope, according to an example implementation.

FIGS. 3-5 and 13 show, in simplified schematic view, a variety of configurations and embodiments of an optical module 110 for imaging fluorophores in a live-cell biological sample 130 using an image sensor 120. The optical module 110 includes filters, light emitters, and other elements configured to provide independently-controllable excitation light in at least three different bands of excitation wavelengths and to pass through light in at least three corresponding bands of emission wavelengths (FIGS. 3, 4, and 5 show three-color configurations and FIG. 13 shows a four-color configuration). The optical module 110 is also configured to pass light from a phase lamp 125 (or other transillumination light source) that has passed through and/or been scattered by the sample 130 to be imaged by the image sensor 120.

The optical module 110 includes a first light source 135 configured to emit a first light in a first band of excitation wavelengths. A first filter 136 is arranged in a first optical path 137 of the first light source 135. The first filter 136 is configured to pass light in one or more wavelengths and to reflect light in one or more other wavelengths. The optical module 110 further includes a second light source 140 configured to emit a second light in a second band of excitation wavelengths. A second filter 141 is arranged in a second optical path 142 of the second light source 140. The second filter 141 is configured to pass light in one or more wavelengths and to reflect light in one or more other wavelengths. The optical module 110 also includes a third light 145 source configured to emit a third light in a third band of excitation wavelengths. A third filter 146 is arranged in a third optical path 147 of the third light source 145. The third filter 146 is configured to pass light in one or more wavelengths and to reflect light in one or more other wavelengths. The direction of excitation light being transmitted to the sample 130 and/or image light (e.g., fluorescent emission light, bright field, phase contrast, or other scatter and/or transmitted image light) being passed through the optical module 110 to the image sensor 120 is indicated in the figures by the arrows on the optical paths.

The filters 136, 141, 146 could include a variety of materials or components configured in a variety of ways to facilitate reflection and/or absorption of certain band(s) of wavelengths and transmission of certain other band(s) of wavelengths. For example, the 136, 141, 146 could be dichroic mirrors composed of many alternating layers of material whose compositions, thicknesses, and ordering can be specified in order to provide a desired passband(s), stopband(s), reflection band(s), or other wavelength-selective optical behaviors.

In the optical module 110, the first optical path 137, the second optical path 142, and the third optical path 147 converge along a primary transmission optical path 150 configured to be directed, via an objective 165, toward the live-cell biological sample 130. The module also includes an emission filter 155 that is located in a primary emission optical path 156 and that is configured to pass light emitted by the fluorophores in the live-cell biological sample 130 in response to being illuminated by the light source(s) 134, 140, 145 and to pass at least some of the light emitted from the phase lamp 125. The primary emission optical path 156 terminates at the imaging sensor 120. The emission filter 155 is configured to pass light in at least first band, a second band and a third band of emission wavelengths that correspond, via respective first, second, and third fluorophores in the sample 130, to the first, second, and third excitation wavelengths emitted by the light sources 134, 140, 145. The emission filter 155 is also configured to pass at least some of the wavelengths of light emitted from the phase lamp 125. In practice, this can include matching the wavelength of the light source(s) of the phase lamp to one or more of the first, second, or third bands of emission wavelengths.

The emission filter 155 may also be configured to reject (e.g., reflect, absorb) light in the first band, the second band and the third band of excitation wavelengths. Alternatively, the reflective action of the other filters 136, 141, 146 may be relied upon to prevent excitation light from the light sources 135, 140, 145 from being received by the image sensor 120. Further, the emission filter 155 may also be configured to reflect or otherwise reject artifactual autofluorescence from the biological sample 130, and/or to reflect light from other fluorescent dyes that may be present in the biological sample 130.

Note that the optical module 110 may include one or both of the objective 165 or the image sensor 120. Alternatively, the optical module 110 may be configured to be removable coupled to one or both of the objective 165 or the image sensor 120. This could be done, e.g., to reduce the cost of individual swappable optical modules.

In an example implementation, shown in FIG. 3, the first filter 136 is configured to pass light in the first band of excitation wavelengths and to reflect light in the second band and the third band of excitation wavelengths and in the first band, the second band and the third band of emission wavelengths as well as a band of wavelengths emitted by the phase lamp 125 (which may overlap with one or more of the first, second, or third bands of emission wavelengths). The second filter 141 is configured to pass light in the third band of excitation wavelengths and in the first band, the second band and the third band of emission wavelengths and the phase lamp wavelengths and to reflect light in the second band of excitation wavelengths. The third filter 146 is configured to pass light in the first band, the second band and the third band of emission wavelengths and the phase lamp wavelengths and to reflect light in the third band of excitation wavelengths.

As shown in FIG. 3, the first light source 135, the second light source 140, and the third light source 145 are arranged in series in the same plane. The arrangement of elements in FIG. 3 results in an optical module 110 that is fairly long in one dimension (horizontally within FIG. 3), while having a smaller dimension in the other two dimensions (vertically, and into and out of the plane of FIG. 3). This may be desirable in some applications. However, in some applications, it may be beneficial to reduce the maximum dimension (s) of the optical module 110 and/or to conform the shape and size of the optical module 110 to a specified shape and/or size (e.g., to fit the module within an incubator, or onto a gantry of an automated imaging system). Accordingly, the arrangement of the elements of the optical module 110 may be modified, e.g., to fold, nest, and/or branch the various optical paths and/or to change the direction and/or ordering of the various optical paths.

In another example implementation, shown in FIG. 4, the first filter 136 is configured to pass light in the first band and the second band of excitation wavelengths and to reflect light in the third band of excitation wavelengths and in the first band, the second band and the third band of emission wavelengths. The second filter 141 is configured to pass light in the second band of excitation wavelengths and to reflect light in the first band of excitation wavelengths. And, the third filter 146 is configured to pass light in the first band, the second band and the third band of emission wavelengths and to reflect light in the third band of excitation wavelengths. Thus, in the implementation shown in FIG. 4, the first light source 135 is arranged such that the first optical path 137 starts at the first light source 135, reflects off of the second filter 141, passes through the first filter 136, and exits the optical module 110 along the primary transmission optical path 150. The second light source 140 is arranged such that the second optical path 142 starts at the second light source 140, passes through the second filter 141 and then through the first filter 136, and exits the optical module 110 along the primary transmission optical path 150. The third light source 145 is arranged such that the third optical path 147 starts at the third light source 145, reflects off of the third filter 146 to the first filter 136, reflects off the first filter 136, and exits the optical module 110 along the primary transmission optical path 150. The primary emission optical path 156 for light emitted by the fluorophores in the live-cell biological sample 130 reflects off the first filter 136, passes through the third filter 146, passes through the emission filter 155, and exits the optical module 110.

In the example implementation of in FIG. 4, the second light source 140 and the third light source 145 are arranged parallel to each other and the first light source 135 is arranged at a ninety degree angle relative to the second light source 140 and the third light source 145. This arrangement permits a more compact optical module 110 that includes the three light sources within the housing 111.

In yet another optional implementation, shown in FIG. 5, the first filter is 136 configured to pass light in the first band of excitation wavelengths. The first filter 136 is also configured to reflect light in the second band and the third band of excitation wavelengths and in the first band, the second band and the third band of emission wavelengths. The second filter 141 is configured to pass light in the first band, the second band, and the third band of emission wavelengths. The second filter 141 is also configured to reflect light in the second band and the third band of excitation wavelengths. And the third filter 146 is configured to pass light in the third band of excitation wavelengths. The third filter 146 is also configured to reflect light in the second band of excitation wavelengths.

Thus, in the implementation shown in FIG. 5, the first light source 135 is arranged such that the first optical path 137 starts at the first light source 135, passes through the first filter 136, and exits the optical module 110 along the primary transmission optical path 150. The second light source 140 is arranged such that the second optical path 142 starts at the second light source 140, reflects off the third filter 146 to the second filter 141, reflects off the second filter 141 to the first filter 136, reflects off the first filter 136, and exits the optical module 110 along the primary transmission optical path 150. The third light source 145 is arranged such that the third optical path 147 starts at the third light source 145, passes through the third filter 146 to the second filter 141, reflects off the second filter 141 to the first filter 136, reflects off the first filter 136 and exits the optical module 110 along the primary transmission optical path 150. Further, the primary emission optical path 156 for light emitted by the fluorophores in the live-cell biological sample 130 reflects off the first filter 136, passes through the second filter 141, passes through the emission filter 155, and exits the optical module 110.

As shown in FIG. 5, the first light source 135 and the third light source 145 are arranged parallel and the second light source 140 is arranged at a ninety degree angle relative to the first light source 135 and the third light source 145. This arrangement permits a more compact optical module 110 that includes the three light sources within the housing 111.

Note that, while the example implementations shown in FIGS. 3-5 and elsewhere herein depict optical modules having light source optical paths that are all entirely in the same plane (i.e., the plane of the figures), other embodiments are possible, e.g., in order to reduce an overall size of the optical module and/or to comport the shape and size of the optical module to an available space (e.g., within a gantry and/or automated intra-incubator imaging apparatus).

For example, the second light source 140 and third filter 146 of the implementation shown in FIG. 5 could be rotated ninety degrees (or some other angle) into (or out of) the plane of FIG. 5. Such an implementation, and additional details thereof, is further illustrated in FIGS. 6-11. As illustrated in FIGS. 6-11, the first, second and third light sources 135, 140, 145, the first, second and third filters 136, 141, 146 and the emission filter 155 are all contained in a housing 111. The housing 111 includes a first opening 112 arranged to permit the primary transmission optical path 150 to pass through to illuminate the biological sample 130. The housing 111 also includes a second opening 113 arranged to permit the primary emission optical path 156 to pass through to the imaging sensor 120. The first and second openings 112, 113 may include optical devices (such as lenses, filters, mirrors, etc.), and/or sensor surfaces. In one optional example, the emission filter 155 may be disposed within the second opening 113. In the example optical module 110, shown in FIGS. 3-8, the housing 111 includes a main body 111a extending vertically and a cantilevered extension 111b extending horizontally therefrom. The main body 111a of the housing 111 includes the first light source 135 and the third light source 145 in the same plane. The cantilevered extension 111b of the housing 111, in turn, includes the second light source 140 arranged at a 90 degree angle relative to the first light source 135 and the second light source 140.

In other words, the second light source 140 and the third filter 146 have been rotated 90 degrees about the vertical axis through the center of the third light source 145. This arrangement places the second light source 140 behind the plane of the first and third light sources 135, 145 such that the second optical path 142 is directed to the third filter 146 where the light is reflected upward. Such an arrangement can be especially beneficial in space-limited applications. For example, the foregoing arrangement permits the optical module to remain compact for integration into an automated, intra-incubator combined epifluorescence and bright field/phase contrast imaging system as described below while also permitting the optical module to be easily swappable by a user, thus expanding the utility and re-configurability of the imaging system.

The light sources 135, 140, 145 discussed herein may each include any device and/or assembly that can send light to or illuminate the biological sample 130. Exemplary light sources may include one or more lamps and associated optics. Exemplary lamps may include incandescent (e.g., halogen or tungsten filament) lamps, arc (e.g., mercury, mercury-xenon, or xenon) lamps, light emitting diodes ("LEDs"), and/or lasers, among others. Associated optics ("source optics") may include an optical fiber and/or liquid light guide, one or more lenses, a filter(s) (such as a polarization or wavelength-based filter), a diffraction grating, a mirror(s), a mask(s), and/or the like. The associated optics may select/adjust the intensity, wavelength, polarization, phase, direction, and/or shape, among others, of light directed to the sample. In one optional implementation, the first light source 135, the second light source 140, and the third light source 145 each include an LED, at least two lenses (e.g., to collimate the light output from the light sources and/or to match the focus of the output light to an infinity focus or other focus of an objective) and a single bandpass dichroic filter.

The specific boundaries of the first, second, third, and/or additional bands of excitation wavelengths emitted from light sources of an optical module may be specified according to an application (e.g., according to the excitation spectrum of available fluorophores or interest, according to the availability of suitable LEDs or other light emitting elements and/or related filters, mirrors, lenses, objectives, or other optical elements). In one optional implementation, the first band of excitation wavelengths ranges from 453 nm to 485 nm and largely corresponds to blue light that causes corresponding fluorophores to emit green (or longer wavelength) light. The second band of excitation wavelengths ranges from 546 nm to 568 nm and largely corresponds to lime light that causes corresponding fluorophores to emit orange (or longer wavelength) light. And, the third band of excitation wavelengths ranges from 648 nm to 674 nm and largely corresponds to red light that causes corresponding fluorophores to emit near infrared (NIR) light. In further implementations, the bounds of the foregoing ranges of this optional embodiment may vary by +/−3 nm.

In another optional implementation, the first band of emission wavelengths ranges from 494 nm to 533 nm and largely corresponds to green light. The second band of emission wavelengths ranges from 576 nm to 639 nm and largely corresponds to orange light. And, the third band of emission wavelengths ranges from 686 nm to 756 nm and largely corresponds to NIR light. In further implementations, the bounds of the foregoing ranges may vary by +/−3 nm.

In some examples, the optical module 110 may include a fourth light source 160 configured to emit a fourth light in a fourth band of excitation wavelengths. An example implementation of such an optical module 110 is shown in FIG. 13. The optical module 110 in this implementation also includes a fourth filter 161 arranged in a fourth optical path 162 of the fourth light source 160. The fourth filter 161 is configured to pass light in one or more wavelengths and to reflect light in one or more wavelengths. And, the emission filter 155 is further configured to pass light in a fourth band of emission wavelengths and reflect light in the fourth band of excitation wavelengths. Adding the fourth light source 160 increases the ability to view a fourth fluorophore in the biological sample 130 and to conduct an even greater number of assays without resort to a separate optical module with different light sources and filters and corresponding configurations.

In the example implementation shown in FIG. 13, the first filter 136 is configured to pass light in the first band of excitation wavelengths and to reflect light in the fourth band of excitation wavelengths. The second filter 141 is configured to pass light in the first band, the second band, the third band, and the fourth band of emission wavelengths and to reflect light in the second band and the third band of excitation wavelengths. The third filter 146 is configured to pass light in the third band of excitation wavelengths and to reflect light in the second band of excitation wavelengths. And, the fourth filter 161 is configured to pass light in the first band and the fourth band of excitation wavelengths and to reflect light in the second band and the third band of excitation wavelengths and in the first band, the second band, the third band and the fourth band of emission wavelengths.

In the example implementation shown in FIG. 13, the first light source 135 is arranged such that the first optical path 137 starts at the first light source 135, passes through the first filter 136 and then through the fourth filter 161, and exits the optical module 110 along the primary transmission optical path 150. The second light source 140 is arranged such that the second optical path 142 starts at the second light source 140, reflects off the third filter 146 to the second filter 141, reflects off the second filter 141 to the fourth filter 161, reflects off the fourth filter 161, and exits the optical module 110 along the primary transmission optical path 150. The third light source 145 is arranged such that the third optical path 147 starts at the third light source 145, passes through the third filter 146 to the second filter 141, reflects off the second filter 141 to the fourth filter 161, reflects off the fourth filter 161, and exits the optical module 110 along the primary transmission optical path 150. The fourth light source 160 is arranged such that the fourth optical path 162 starts at the fourth light source 160, reflects off the first filter 136, passes through the fourth filter 161, and exits the optical module 110 along the primary transmission optical path 150. And, the primary emission optical path 156 for light emitted by the fluorophores in the live-cell biological sample 130 reflects off the fourth filter 161, passes through the second filter 141, passes through the emission filter 155, and exits the optical module 110. As shown in FIG. 13, the first light source 135 and the third light source 145 are arranged parallel to each other and the second light source 140 and the fourth light source 160 are each arranged at a ninety degree angle relative to the first light source 135 and the third light source 145. This arrangement permits a compact optical module 110 that includes the four light sources within the housing 111.

Such a fourth band of emission wavelengths may include wavelengths shorter than 453 nm and may largely correspond to violet light and the corresponding fourth band of emission wavelengths may largely correspond to blue light.

IV. Example System

In a second aspect of the disclosure, shown in FIGS. 1, 3, 4, 5, and 13, a system 105 is provided for assaying live-cell biological samples 130. The system 105 includes the optical module 110 according the first aspect of the disclosure. The system 105 also includes a fluorescence microscope 115 that encompasses the optical module 110 and to which the optical module 110 is removably coupled. The fluorescence microscope 115 has at least one objective 165. The system 105 further includes the imaging sensor 120 arranged in the primary emission optical path for light emitted by the fluorophores in the live-cell biological sample 130 and/or light from the phase lamp 125 (or other transillumination light source, e.g., a light source configured to provide illumination for bright-field imaging but not for phase contrast imaging) transmitted through and/or scattered by the sample 130 from the objective 165. And, the system 105 includes a phase lamp 125 removably coupled to the fluorescence microscope 115 and arranged at a terminating end of the primary transmission optical path 150.

The fluorescence microscope 115, as used herein, is any optical device that magnifies the image of small objects, such as cells, organelles, tissues, small organisms, particles, etc. Exemplary modes of microscopy that may be performed by the detection mechanism include optical microscopy (for example, brightfield, darkfield, phase-contrast, differential interference contrast (such as Nomarski, DIC, and Hoffman Modulation Contrast), fluorescence, and/or other forms of visible and/or invisible (e.g., IR, NIR, ultraviolet) light microscopy. The objective 165 is arranged between the optical module 110 and the biological sample 130 such that the primary optical transmission path 150 and the primary optical emission path 156 pass through the objective 165.

The imaging sensor 120 is configured to detect light and can include a camera, a multi-channel photodetector, a planar Fourier capture array, a single-pixel imager, or some other image-generating apparatus. The imaging sensor 120 can be configured or operated to detect light at a range of wavelengths. For example, the imaging sensor 120 is configured or operated to detect light at multiple wavelengths/ranges of wavelengths corresponding to emission spectra of fluorescent dyes or other fluorophores in the biological sample 130. For example, these wavelengths may correspond to peaks in the emission spectra of multiple fluorophores in the sample and/or extend across a broad range of wavelengths. This could include the imaging sensor 120 being a monochrome imaging sensor that is sensitive to wavelengths of light in each of the emission spectra and/or wavelengths of light emitted by a phase lamp or other transillumination source. Still further, the imaging sensor 120 may be configured to measure any suitable photoluminescence including fluorescence intensity (FLINT), fluorescence resonance energy transfer (FRET), fluorescence lifetime (FLT), fluorescence correlation (FCS), fluorescence recovery after photobleaching (FRAP), and their phosphorescence and other analogs, among others.

In one optional implementation, shown in FIGS. 6-8 and 11-12, the system 105 includes a shaft 170 extending through the optical module 110. Here, the fluorescence microscope 115 has a receptacle (not shown) configured to receive the shaft 170 in a first orientation. And, the shaft 170 is configured to rotate under the application of a force to a second orientation thereby locking the optical module 110 to the rest of the fluorescence microscope 115 (e.g., to a housing or other elements of the fluorescence microscope 115). For example, the shaft 170 may have a flip tab 171 coupled to a first end 172 and may have protrusions 173 coupled to a second end 174 thereby forming a T-shape. The fluorescence microscope 115 may have a corresponding slot (not shown) and receptacle configured to receive the T-shaped protrusions 173 in a first orientation. When the shaft rotates to the second orientation under the application of a force to the flip tab 171, the T-shaped protrusions 173 rotate in the receptacle such that the T-shape protrusions 173 are in opposition to the slot thereby locking the optical module 110 to the fluorescence microscope 115. Once the optical module 110 is coupled to the rest of the fluorescence microscope 115, the flip tab 171 may be folded flat against the housing 111.

In a further implementation, once the shaft 170 is inserted, rotation of the shaft 170 in the locking direction causes the protrusions 173 to ride along a ramp pulling them, the shaft 170 and the optical module 110 onto mounts for the rest of the system 105. Compliant elements (e.g. a spring 189) may be arranged between the shaft 170 and the housing 111 of optics module 110 to control the force pulling the optics module 110 onto the mounts. In addition, detents may provide tactile feedback when the shaft 170 is in the locked and unlocked positions.

In another optional implementation, shown in FIG. 4, the system 105 includes a first electrical connector 175 coupled to the optical module 110. The system 105 includes a second electrical connector (not shown) coupled to the rest of the fluorescence microscope 115. The second electrical connector is reciprocal with the first electrical connector 175. And, the system 105 includes a processor 202 in electrical communication with the second electrical connector. The processor 202 configured to identify the optical module 110 coupled to the rest of the fluorescence microscope 115. The first and second electrical connectors 175 may be selected to require less than a specified force to connect and disconnect, e.g., to make it easier for a user to swap different optical modules of the fluorescence microscope 115.

A swappable phase lamp module 125 includes a housing 126, a transillumination light source 127 (e.g., a halogen lamp, an LED), and at least one condenser lens which focuses light from the phase lamp module 125 onto the biological sample 130 from above. In yet another optional implementation, shown in FIGS. 14-15, the phase lamp module 125 has a third electrical connector 177 that corresponds to a fourth electrical connector (not shown) that is coupled to the rest of the fluorescence microscope 115 (e.g., to the same housing to which the second electrical connector is coupled). The third electrical connector 177 is reciprocal with the fourth electrical connector. The processor 202 is configured to determine whether the optical module 110 and the phase lamp module 125 are compatible and to cause an alert to be displayed in response to the determination that they are not compatible. Such a determination may be made by performing a lookup in a database that contains a record of valid correspondences between available optical modules 110 and available phase lamp modules 125. Additionally or alternatively, such a determination may be made by comparing a set of wavelengths of light emitted by the phase lamp module 125 with a set of wavelengths of light that the optical module 110 is configured to pass from the sample 130 to the imaging sensor 120.

The housing 126 of the phase lamp module 125 includes a protrusion 128 shaped to be received into a corresponding receptacle 186 in a phase lamp mount 185 of the system 105.

The protrusion 128 and receptacle 186 are shaped in such a way that the phase lamp module 125 can only be installed in a single orientation. Rather than being secured with a screw, the phase lamp module 125 is held in place by a detent 187. The detent 187 is in the form of spring-loaded balls 188 in the phase lamp mount 185 configured to align with grooves 129 in the protrusion 128 of the housing 126.

In one optional implementation, shown in FIG. 1, the system 105 includes an incubator 180 configured to maintain the live-cell biological samples 130 at a temperature ranging from 30° C. to 42° C. and at a relative humidity ranging from 80% to 100%. In this implementation, the fluorescence microscope 115 according to the first aspect of the disclosure is coupled to a chamber of the incubator 180. In another implementation, the fluorescence microscope 115 may be contained partially or entirely within the incubator 180. For example, the fluorescence microscope 115 may be disposed entirely within a standard $CO_2$ incubator for time-lapsed examination of the biological sample 130 during continuous culture (e.g., over a specified period of hour(s), day(s), or week(s)). Due to the length of the incubation time, the fluorescence microscope 115 may remain in the incubator during cell culture to avoid adversely affecting the biological sample 130. In addition, the compact profile of the fluorescence microscope 115 maintains the functionality of the incubator 180 for placement of other biological samples 130 in the open space around the fluorescence microscope 115. The fluorescence microscope's 115 compact profile also reduces air flow restrictions that can have detrimental effects in the form of condensation and improper aeration on the fluorescence microscope 115 or the biological samples 130.

The third light source 145 (and fourth light source 160) enables multiplexing assays on a biological sample 130 to conduct multiple assays and/or fluorescent indicators in individual samples (e.g., sample wells) in the incubator 180 and/or in sets of different samples in the same incubator 180.

V. Example Methods

Referring now to FIG. 16, a method 300 is illustrated that may utilize the optical module 110 and system 105 of FIGS. 3-15 and computing device 200 of FIGS. 1-2 for imaging fluorophores in live-cell biological samples. Method 300 includes, at block 305, aligning a first biological sample and a fluorescence microscope such that the first biological sample is located within a field of view of the fluorescence microscope, wherein the first biological sample contains (i) a first fluorophore that emits light in a first band of emission wavelengths in response to illumination by light in first band of excitation wavelengths, (ii) a second fluorophore that emits light in a second band of emission wavelengths in response to illumination by light in second band of excitation wavelengths, and (iii) a third fluorophore that emits light in a third band of emission wavelengths in response to illumination by light in third band of excitation wavelengths. Then, at block 310, the method includes obtaining a set of images of the first biological sample using the fluorescent microscope, wherein the images of the set of images differ with respect to focus setting. Next, at block 315, the method 300 includes determining, based on the set of images, first, second, and third in-focus settings for the first, second, and third bands of emission wavelengths, respectively. And at block 320, the method includes, during a first period of time, using a first light source to illuminate the first biological sample with light in the first band of excitation wavelengths and operating the fluorescence microscope according to the first in-focus setting to obtain, via an image sensor of the fluorescence microscope, a first image of light in the first band of emission wavelengths. The method 300 also includes, at block 325, during a second period of time, using a second light source to illuminate the first biological sample with light in the second band of excitation wavelengths and operating the fluorescence microscope according to the second in-focus setting to obtain, via the image sensor, a second image of light in the second band of emission wavelengths. The method 300 also includes, at block 330, during a third period of time, using a third light source to illuminate the first biological sample with light in the third band of excitation wavelengths and operating the fluorescence microscope according to the third in-focus setting to obtain, via the image sensor, a third image of light in the third band of emission wavelengths. All of the foregoing steps may be performed automatically by processor 202.

Obtaining a particular fluorescent image for a particular color could include operating the imaging system to generating a plurality of different images of the particular color using different exposure times. This could be done to allow the synthetic generation of high dynamic range images. This could be done for fluorophores/samples/assays that exhibit very high variations in the intensity of fluorescent emission across a range of fluorophore concentrations/activities of interest.

The method 300 could additionally include obtaining one or more bright field, phase contrast, or other non-fluorescent images by operating a phase lamp (e.g., 125) or other transillumination light source. Such non-fluorescent image information could then be used in combination with the fluorescent images (e.g., using phase contrast imagery to identify the locations, shapes, sizes, and/or extents of cells in the sample regardless of cell type, and then using one or more fluorescent images to determine the cell type, phase of cell division, cell health, cell metabolic activity, or other information about the cells identified using the phase contrast imagery) or on its own.

Further, method 300 could include obtaining a set of bright field, phase contrast, or other non-fluorescent images across a range of different focus settings (e.g., across a range of different objective-sample distances) in order to determine the in-focus settings for the three (or more) fluorescent images obtained using method 300. This could include determining an in-focus setting for the wavelength of illumination used to generate the non-fluorescent images and then applying known offsets (e.g., distance offsets), from that in-focus setting, for each of the imaged fluorescent emission wavelengths to determine the in-focus settings for those emission wavelengths. Where the wavelength of wavelength of illumination used to generate the non-fluorescent images is the same or substantially the same as one of the fluorescent emission wavelengths, the offset could be zero. Bright field images or other non-fluorescent images often contain significantly more image data for the same exposure time when compared to fluorescent images, so this method of determining in-focus settings can advantageously reduce the time needed to generate such in-focus settings. This can also reduce the amount of photobleaching that a sample experiences in order to generate such in-focus settings.

In practice, images of fluorophores excited by shorter wavelengths can include artifacts related to light emitted from fluorophores excited by longer wavelengths and vice versa. As one example, the fluorophores corresponding to the first band of wavelengths may also be excited to some degree by the second and third bands of wavelengths (especially if the second and third bands of wavelengths include shorter wavelengths than the first band of wavelengths). Likewise, the fluorophores corresponding to the second band of wavelengths may also be excited to some degree by the first and third bands of wavelengths, while the fluorophores corresponding to the third band of wavelengths may also be excited to some degree by the first and second bands of wavelengths.

To address the artifact issue, in one optional implementation, method 300 further includes the processor 202 that is in electrical communication with the imaging sensor 120 (or some other computing device) generating a first image of light emitted by a first fluorophore based on the first set of images in order to reduce artifacts from light emitted by a second fluorophore and a third fluorophore. The processor 202 additionally generates a second image of light emitted by the second fluorophore based on the second set of images in order to reduce artifacts from light emitted by the first fluorophore and the third fluorophore. Yet further, the processor 202 can generate a third image of light emitted by the third fluorophore based on the third set of images in order to reduce artifacts from light emitted by the first fluorophore and the second fluorophore. This spectral unmixing process is described in more detail with respect to two excitation wavelengths in U.S. patent application Ser. No. 16/264,819 filed on Feb. 1, 2019 and incorporated herein by reference.

In one non-limiting example, the first image could be obtained for a green fluorophore by illuminating a biological sample 130 with light at a blue excitation wavelength corresponding to the green fluorophore, when the biological sample 130 is arranged at a first in-focus setting such that the light emitted from the green fluorophore is in focus. Specifically, the "in-focus setting" occurs by setting a distance between the biological sample 130 and the objective 165 of the fluorescence microscope 115 such that the green fluorophore emission light is imaged in-focus. This first image may also include light emitted from orange fluorophores (primarily excited by light at a lime excitation wavelength, but also excited to some degree by the blue light) and NIR fluorophores (primarily excited by light at a red excitation wavelength, but also excited to some degree by the blue light) in the biological sample 130. Note that the light emitted from the orange and NIR fluorophores will be out of focus in the first image. This is due to chromatic aberration caused by elements along the primary emission optical path 156 between the sample 130 and the imaging sensor 120 (e.g., the objective, a tube lens, the optical properties of the sample and/or of the containers containing the sample).

Artifact images can then be removed from the first image to remove the artifact light from the orange and NIR fluorophores. As noted above, one artifact image may be obtained by illuminating the biological sample 130 with light at a lime excitation wavelength corresponding to the orange fluorophore at the first in-focus setting used to obtain the first image. Another artifact image may be obtained by illuminating the biological sample 130 with light at a red excitation wavelength corresponding to the red fluorophore at the first in-focus setting used to obtain the first image. Alternatively, the artifact images may be obtained by blurring in-focus images of the orange and red fluorophores or otherwise applying some image processing techniques to simulate the effect of the focus setting used to obtain the first image in an image taken using another focus setting. For example, images taken using in-focus settings such that the light emitted from the orange and NIR fluorophores are separately imaged in-focus.

In one optional implementation, method 300 further includes an incubator containing or otherwise coupled to the fluorescence microscope that maintains at least the first biological sample at a temperature ranging from 30° C. to 42° C. and at a relative humidity ranging from 80% to 100%, when obtaining the first set of image data, the second set of image data, and the third set of image data. This data can be obtained within a standard $CO_2$ incubator for time-lapsed examination of the biological sample 130 during continuous culture (e.g., over a period of minute(s), hour(s), day(s), or week(s), depending on the experiment of interest). For example, images could be taken over time throughout a culture that is longer than 14 days, or that is as long as or longer than 30 days.

The method 300 could include performing some additional analysis on the fluorescent images and/or other images obtained using the system (e.g., bright field images, phase contrast images). For example, where one (or more) of the images correspond, in a particular sample, to the color of fluorophores that are specific to a particular type or types of cells, then the method 300 could include analyzing the image(s) to determine the number, shapes, sizes, distributions, pattern of interconnection, or other information about cells of the particular type or types that are present in the sample. Such an identification could be augmented by the use of phase contrast or other non-fluorescent images to identify the location, shape, and extent of individual cells in the sample, regardless of type. Additionally or alternatively, where one (or more) of the images correspond to a fluorescent indicator of a particular assay (e.g., an Annexin V NIR assay, a two- or three-color FUCCI cell division phase assay), then the method 300 could include analyzing the image(s) to generate output(s) of the particular assay, e.g., to determine a health, phase of cell division, or other metabolic state or status of one or more cells in the sample. The results of different analyses of different (or overlapping) images could be combined, e.g., a first image analysis, corresponding to a cell-specific fluorophore, could be used to identify cells of a cell type of interest and a combined second and third image analysis could determine the output of a two-color assay (e.g., a two-color FUCCI assay) for the identified cells. The analyses could be the same for every sample that is imaged by an imaging system in an incubator (e.g., due to all of the samples containing the same assays/fluorescent indicator/dyes), or could differ from sample to sample within the incubator.

In one optional implementation, the method 300 further includes the processor 202 identifying a first cell type in a first biological sample based on the first set of images. Then, the processor 202 identifies a second cell type in the first biological sample based on the second set of images. Next, the processor 202 identifies cell death or some other metabolic process or property in the first biological sample based on the third set of images. This has the technical effect of permitting complicated assays and/or multiple assays to be run in a single vessel in the system 105 without changing the configuration of the optical module 110.

In one optional implementation phase contrast, brightfield, or other non-fluorescent images may be obtained at the first, second, and third in-focus settings. These images may be utilized to remove further artifacts from the first, second and third images (e.g., to remove artifacts due to autofluorescence) or to otherwise improve the first, second, and third images (e.g., by providing additional high-spatial-frequency image data to augment the fluorescent images).

In one optional implementation, the method 300 also includes the processor receiving compatibility information for the optical module 110 and the phase lamp module. Then, the processor 202 determines whether the optical module 110 and the phase lamp 125 are compatible based on the compatibility information. Next, in response to a determination that the optical module 110 and the phase lamp 125 are incompatible, the processor 202 causes an alert to be displayed with an indication of incompatibility. Such a compatibility determination may be made by performing a lookup in a database that contains a record of valid correspondences between available optical modules 110 and available phase lamp modules 125. Additionally or alternatively, such a determination may be made by comparing a set of wavelengths of light emitted by the phase lamp module 125 with a set of wavelengths of light that the optical module 110 is configured to pass from the sample 130 to the imaging sensor 120.

In one optional implementation, the method 300 includes extending a shaft 170 in a first orientation through the optical module 110 to a receptacle in a fluorescence microscope 115. Then, the shaft 170 is rotated under the application of a force such that shaft 170 moves to a second orientation thereby coupling the optical module 110 to the fluorescence microscope 115, as described in detail above with respect to the system 105.

The foregoing method 300 has the technical effect of permitting increased variability in the assays that can be run in individual vessels or across multiple vessels in the system 105 without changing the configuration of the optical module 110. The method 300 may be performed by, or in combination with, any of the embodiments of fluorescent imagers, optical modules, phase lamp modules, incubators, automated imaging systems, or other systems, devices, or components described herein. A variety of assays, fluorescent indicators, and combinations thereof in individual samples within an incubator and/or across different samples within an incubator are thus made possible by the embodiments described herein. A number of examples of such applications are provided below. These applications are intended as illustrative embodiments and are not intended to be limiting. Additional or alternative applications are anticipated, as are additional or alternative combinations of such applications and/or of the applications described below.

As discussed above, a non-transitory computer-readable medium having stored thereon program instructions that upon execution by a processor 202 may be utilized to cause performance of any of the methods described herein.

VI. Example Biological Applications

The embodiments described above, by providing for the independent imaging of three different fluorescence channels, enable a variety of applications in fluorescence imaging. The advantages of an additional fluorescence channel can include improving the throughput of a single imaging apparatus by allowing additional assays to be performed simultaneously using a single apparatus (e.g., in a single incubator), by providing flexibility in experimental readouts across different samples and/or by allowing additional assays to be performed from individual samples. The availability of three (or more) color imaging may also allow for increased flexibility in reagent selection, e.g., the ability to use multiple reagents to gain additional information while monitoring cells expressing green fluorescent protein-based reporters.

Additionally or alternatively, simultaneous three (or more) color imaging may permit information to be generated that could not be generated using only two colors. For example, information from a three-color reporter (e.g., a three-color FUCCI assay) could be generated. In another example, information about the proliferation and interaction of multiple cell types as well as metabolic or cell death information across cell populations could be generated. Such information could enable additional insight into the effects of experimental conditions on the activity of the effector cells in destroying target cells or metabolic exchange between, e.g., cancer and stromal cells.

Yet further, three (or more) color imaging may allow for the generation of experimental data in a higher-confidence manner. For example, multiplexing multiple readouts in a single sample may provide increased confidence that differences observed between the readouts are scientifically valid and not due to experimental variations (e.g., cell plating) between assays run in parallel.

Example 1: 2-Color FUCCI+Cell Death

Various implementations of the optical module 110, system 105 and methods 300 described herein can be advantageously used to conduct two-color cell cycle (e.g., Green/Orange FUCCI) observation and cell death analysis in a single sample. Cell cycle and apoptosis readouts may demonstrate differential concentration- and time-dependent effects of compounds in cancer cells, for example. In another example, two-color cell cycle observation and cell death analysis could be performed in a sample containing immune cells and cancer cells in order to observe the effects of targeted immune cell killing of cancer cells on the cancer cells and/or on some other population of cells in the sample. Multiplexing these two readouts in a single sample increases throughput and provides confidence that differences between the two readouts are scientifically valid and not due to experimental variation between parallel assays.

With respect to the two color FUCCI analysis, the three-color optical module of the present disclosure permits differentiation between the various cell cycle phases based on phase-dependent expression of two different fluorescent proteins. For example, during S, G2, and M phases, cells could emit Green fluorescence via expression of TagGFP2 (a green fluorophore) that can be detected using the three-color optical module. During the G1 phase and transition into S phase, cells could emit orange fluorescence via expression of TagRFP (an orange fluorescent protein that possesses bright fluorescence with excitation/emission maxima at 555 and 584 nm, respectively) that can be detected using the three-color optical module. In this two-color FUCCI assay, cells transition through a colorless period immediately following mitosis. As a result, cell cycle phases have fluorescence footprints (e.g., S, G2, and M phases: Green; G1 phase: Orange, G1/S transition: both Orange and Green; M/G1 transition: colorless (no fluorescence). The third color can then be used to image a fluorescent cell death readout (e.g., an Annexin V NIR apoptosis indicator).

Example 2: 3-Color FUCCI

Various implementations of the optical module 110, system 105 and methods 300 described herein can be used to advantageously conduct a three-color FUCCI assay independently observing additional phases within the cell cycle. Unlike the two-color cell cycle assay described previously, the three-color assay permits differentiation between the S phase and the G2 phase, and also beneficially results in no colorless phase by appropriate genetic expression of genes for fluorescent proteins fused to targeted ubiquitinylation domains or other cell-phase related targets. For example, during the S phase, G2 phase, and M phase cells could each emit green fluorescence based on the expression of TagGFP2 which can be detected using the three-color optical module, with dimmer fluorescence observed in S phase. And different fluorescence markers can be used to identify other stages of the cell cycle, including, but not limited to, TagRFP and iRFP713. During the G1 phase and S phase, cells expressing TagRFP emit Orange fluorescence that can be detected using the three-color optical module. iRFP713 is a near-infrared fluorescent protein that possesses fluorescence with excitation/emission maxima at 690 and 713 nm, respectively. During the G2 phase, M phase, and G1 phase, cells expressing iRFP713 emit NIR fluorescence, which can be detected using the three-color optical module. As a result, cell cycle phases would have fluorescence footprints (e.g., G2 and M phases: Green and NIR; G1 phase: Orange and NIR, S phase: Orange and Green), with no colorless phase present.

Example 3: 3-Color Immune Cell Killing

Various implementations of the optical module 110, system 105 and methods 300 described herein can be used to advantageously monitor labelled target (cancer) cells and effector (immune) cells and to provide a cell death readout across both cell types. This provides the benefit of being able to independently measure the proliferation and interaction of the target and effector cells simultaneously with cell death across both populations. In this manner the efficacy of immune cell killing of target cells can be directly correlated with changes in effector population (e.g., associated with activation) and interactions between the two cell populations in the same sample, measured by determining overlap between the fluorescence of the effector and target cell labels.

In general, immune-cell recognition and killing of unwanted target cells, such as emergent tumor cells, is a critical component of the human host defense mechanism. Antibody-dependent cell-mediated cytotoxicity (ADCC) and T cell killing are two mechanisms of cell-mediated immune response. Each of these processes involves the stimulation of immune cell sub-populations, such as natural killer (NK) cells or cytotoxic T lymphocytes (CTL), which then actively lyse target cells. The systems and methods of the present disclosure permit observation of the interplay between immune and cancer cells, potentially providing information leading to the development of diagnostics and therapies for restoring and promoting the immune system's capacity to fight and eliminate tumors ("cancer immunotherapy" or "immuno-oncology").

Example 4: ATP+Cell Death

Various implementations of the optical module 110, system 105 and methods 300 described herein can be used to advantageously conduct a two-color Forster resonance energy transfer (FRET)-based measurement of ATP multiplexed with cell death analysis to investigate possible differences in the time- and concentration-dependent effects of compounds on the metabolism and mortality of cancer cells. In operation, three light sources in the optical module may be activated in three different bands of excitation wavelengths, two of which are used to measure, via a FRET mechanism, metabolism information via a single emission band. The third excitation wavelength can then be used to monitor an independent readout related to cell death (e.g., Annexin V NIR). The ATP measurement process is described in more detail in PCT/US19/21171, "Methods and Compositions for Live Cell Analysis of Intracellular ATP," filed on Mar. 7, 2019 and incorporated herein by reference in its entirety.

Example 5: Live-Cell Immunocytochemistry

Various implementations of the optical module 110, system 105 and methods 300 described herein can be used to measure surface protein expression by live cell immunocytochemistry (ICC) using IncuCyte® FabFluor Antibody Labeling Reagent (or some other fluorescently-labelled antibody reagent). This method may be used to track changes in cell subpopulations following experimental treatments (e.g., addition of test compounds or immune cell activation), monitor changes in differentiation markers over time, or otherwise evaluate surface protein expression. Three (or more) color imaging provides advantages in flexibility of antibody selection and enables monitoring of additional proteins or subpopulations of interest in a single sample.

The description of different advantageous arrangements has been presented for purposes of illustration and description, and is not intended to be exhaustive or limited to the examples in the form disclosed. Many modifications and variations will be apparent to those of ordinary skill in the art. The example or examples selected are chosen and described in order to best explain the principles of the examples, the practical application, and to enable others of ordinary skill in the art to understand the disclosure for various examples with various modifications as are suited to the particular use contemplated.

We claim:

1. An optical module for imaging fluorophores in a live-cell biological sample, comprising:
    a first light source configured to emit a first light in a first band of excitation wavelengths;
    a first filter arranged in a first optical path of the first light source, the first filter is configured to pass light in one or more wavelengths and to reflect light in one or more wavelengths;
    a second light source configured to emit a second light in a second band of excitation wavelengths;
    a second filter arranged in a second optical path of the second light source, the second filter is configured to pass light in one or more wavelengths and to reflect light in one or more wavelengths;
    a third light source configured to emit a third light in a third band of excitation wavelengths;
    a third filter arranged in a third optical path of the third light source, the third filter is configured to pass light in one or more wavelengths and to reflect light in one or more wavelengths, wherein the first optical path, the second optical path, and the third optical path converge along a primary transmission optical path configured to be directed toward the live-cell biological sample; and
    an emission filter arranged in a primary emission optical path for light emitted by the fluorophores in the live-cell biological sample, wherein the primary emission optical path is configured to terminate at an imaging sensor, where the emission filter is configured to pass light in a first band, a second band and a third band of emission wavelengths and is configured to reflect light in the first band, the second band and the third band of excitation wavelengths,
    wherein the first filter is configured to pass light in the first band of excitation wavelengths and to reflect light in the second band and the third band of excitation wavelengths and in the first band, the second band and the third band of emission wavelengths,
wherein the second filter is configured to pass light in the first band, the second band, and the third band of emission wavelengths and to reflect light in the second band and the third band of excitation wavelengths, and
wherein the third filter is configured to pass light in the third band of excitation wavelengths and to reflect light in the second band of excitation wavelengths.

2. The optical module of claim 1, wherein the first filter, the second filter and the third filter are each a dichroic filter.

3. The optical module of claim 1, wherein the first light source, the second light source and the third light source each include an LED, at least one lens and a single bandpass dichroic filter.

4. The optical module of claim 1, wherein the first light source is arranged such that the first optical path starts at the first light source, passes through the first filter and exits the optical module along the primary transmission optical path,
wherein the second light source is arranged such that the second optical path starts at the second light source, reflects off the third filter to the second filter, reflects off the second filter to the first filter, reflects off the first filter and exits the optical module along the primary transmission optical path,
wherein the third light source is arranged such that the third optical path starts at the third light source, passes through the third filter to the second filter, reflects off the second filter to the first filter, reflects off the first filter and exits the optical module along the primary transmission optical path, and
wherein the primary emission optical path for light emitted by the fluorophores in the live-cell biological sample reflects off the first filter, passes through the second filter, passes through the emission filter, and exits the optical module.

5. The optical module of claim 1, wherein the first filter is configured to pass light in the first band and the second band of excitation wavelengths and to reflect light in the third band of excitation wavelengths and in the first band, the second band and the third band of emission wavelengths,
wherein the second filter is configured to pass light in the second band of emission wavelengths and to reflect light in the first band of excitation wavelengths, and
wherein the third filter is configured to pass light in the first band, the second band and the third band of emission wavelengths and to reflect light in the third band of excitation wavelengths.

6. The optical module of claim 5, wherein the first light source is arranged such that the first optical path starts at the first light source, reflects off the second filter, passes through the first filter, and exits the optical module along the primary transmission optical path,
wherein the second light source is arranged such that the second optical path starts at the second light source, passes through the second filter and then through the first filter, and exits the optical module along the primary transmission optical path,
wherein the third light source is arranged such that the third optical path starts at the third light source, reflects off the third filter to the first filter, reflects off the first filter, and exits the optical module along the primary transmission optical path, and
wherein the primary emission optical path for light emitted by the fluorophores in the live-cell biological sample reflects off the first filter, passes through the third filter, passes through the emission filter, and exits the optical module.

7. The optical module of claim 1, wherein the first band of excitation wavelengths ranges from 453 nm to 485 nm, wherein the second band of excitation wavelengths ranges from 546 nm to 568 nm, and wherein the third band of excitation wavelengths ranges from 648 nm to 674 nm.

8. The optical module of claim 1, wherein the first band of emission wavelengths ranges from 494 nm to 533 nm, the second band of emission wavelengths ranges from 576 nm to 639 nm, and the third band of emission wavelengths ranges from 686 nm to 756 nm.

9. The optical module of claim 1, further comprising:
a fourth light source configured to emit a fourth light in a fourth band of excitation wavelengths; and
a fourth filter arranged in a fourth optical path of the fourth light source, the fourth filter is configured to pass light in one or more wavelengths and to reflect light in one or more wavelengths, wherein the emission filter is further configured to pass light in a fourth band of emission wavelengths and reflect light in the fourth band of excitation wavelengths.

10. The optical module of claim 9, wherein the first filter is configured to pass light in the first band of excitation wavelengths and to reflect light in the fourth band of excitation wavelengths,
wherein the second filter is configured to pass light in the first band, the second band, and the third band of emission wavelengths and to reflect light in the second band and the third band of excitation wavelengths,
wherein the third filter is configured to pass light in the third band of excitation wavelengths and to reflect light in the second band of excitation wavelengths, and
wherein the fourth filter is configured to pass light in the first band and the fourth band of excitation wavelengths and to reflect light in the second band and the third band of excitation wavelengths and in the first band, the second band, the third band and the fourth band of emission wavelengths.

11. The optical module of claim 1, wherein the first light source is arranged such that the first optical path starts at the first light source, passes through the first filter and then through the fourth filter, and exits the optical module along the primary transmission optical path,
wherein the second light source is arranged such that the second optical path starts at the second light source, reflects off the third filter to the second filter, reflects off the second filter to the fourth filter, reflects off the fourth filter, and exits the optical module along the primary transmission optical path,
wherein the third light source is arranged such that the third optical path starts at the third light source, passes through the third filter to the second filter, reflects off the second filter to the fourth filter, reflects off the fourth filter, and exits the optical module along the primary transmission optical path,
wherein the fourth light source is arranged such that the fourth optical path starts at the fourth light source, reflects off the first filter, passes through the fourth filter, and exits the optical module along the primary transmission optical path, and
wherein the primary emission optical path for light emitted by the fluorophores in the live-cell biological sample reflects off the fourth filter, passes through the second filter, passes through the emission filter, and exits the optical module.

12. The optical module of claim 9, wherein the fourth band of emission wavelengths is less than 453 nm and the fourth band of excitation wavelengths is less than the fourth band of emission wavelengths.

13. A system for assaying live-cell biological samples, the system comprising:
the optical module of claim 1;
a fluorescence microscope removably coupled to the optical module, wherein the fluorescence microscope has at least one objective;
the imaging sensor arranged in the emission path for light emitted by the fluorophores in the live-cell biological sample from the objective; and
a phase lamp removably coupled to the fluorescence microscope and arranged at a terminating end of the primary transmission optical path.

14. The system of claim 13, further comprising:
a shaft extending through the optical module, wherein the fluorescence microscope has a receptacle configured to receive the shaft in a first orientation, wherein the shaft is configured to rotate under the application of a force to a second orientation thereby locking the optical module to the fluorescence microscope.

15. The system of claim 13, further comprising:
a first electrical connector coupled to the optical module;
a second electrical connector coupled to the fluorescence microscope, wherein the second electrical connector is reciprocal with the first electrical connector; and
a processor in electrical communication with at least one of the first electrical connector and the second electrical connector, the processor configured to identify the optical module coupled to the fluorescence microscope.

16. The system of claim 15, further comprising:
the phase lamp having a third electrical connector; and
a fourth electrical connector coupled to the fluorescence microscope, wherein the third electrical connector is reciprocal with the fourth electrical connector, wherein the processor is configured to determine whether the optical module and the phase lamp are compatible and to cause an alert to be displayed in response to that determination.

17. The system of claim 13, further comprising:
an incubator configured to maintain the live-cell biological samples at a temperature ranging from 30° C. to 42° C. and at a relative humidity ranging from 80% to 100%, wherein the optical module of claim 1 is coupled to a chamber of the incubator.

18. A method for imaging fluorophores in live-cell biological samples, comprising:
aligning a first biological sample and a fluorescence microscope such that the first biological sample is located within a field of view of the fluorescence microscope, wherein the first biological sample contains (i) a first fluorophore that emits light in a first band of emission wavelengths in response to illumination by light in first band of excitation wavelengths, (ii) a second fluorophore that emits light in a second band of emission wavelengths in response to illumination by light in second band of excitation wavelengths, and (iii) a third fluorophore that emits light in a third band of emission wavelengths in response to illumination by light in third band of excitation wavelengths;
obtaining a set of images of the first biological sample using the fluorescent microscope, wherein the images of the set of images differ with respect to focus setting;
determining, based on the set of images, first, second, and third in-focus settings for the first, second, and third bands of emission wavelengths, respectively;
during a first period of time, using a first light source to illuminate the first biological sample with light in the first band of excitation wavelengths and operating the fluorescence microscope according to the first in-focus setting to obtain, via an image sensor of the fluorescence microscope, a first image of light in the first band of emission wavelengths;
during a second period of time, using a second light source to illuminate the first biological sample with light in the second band of excitation wavelengths and operating the fluorescence microscope according to the second in-focus setting to obtain, via the image sensor, a second image of light in the second band of emission wavelengths; and
during a third period of time, using a third light source to illuminate the first biological sample with light in the third band of excitation wavelengths and operating the fluorescence microscope according to the third in-focus setting to obtain, via the image sensor, a third image of light in the third band of emission wavelengths.

19. The method of claim 18, further comprising:
generating, via a processor in electrical communication with the imaging sensor, a first corrected image of light emitted by the first fluorophore based on the first, second, and third images in order to reduce artifacts from light emitted by the second fluorophore and the third fluorophore;
generating, via the processor, a second corrected image of light emitted by the second fluorophore based on the first, second, and third images in order to reduce artifacts from light emitted by the first fluorophore and the third fluorophore; and
generating, via the processor, a third corrected image of light emitted by the third fluorophore based on the first, second, and third images in order to reduce artifacts from light emitted by the first fluorophore and the second fluorophore.

20. The method of claim 18, further comprising:
maintaining, via an incubator coupled to the fluorescence microscope, at least the first biological sample at a temperature ranging from 30° C. to 42° C. and at a relative humidity ranging from 80% to 100%, when obtaining the first, second, and third images.

21. The method of claim 18, further comprising generating a first corrected image based on a phase or bright-field image obtained when the first biological sample is at the first in-focus setting and the first image.

22. The method of claim 18, further comprising:
receiving, via a processor, compatibility information for an optical module and a phase lamp module of the fluorescence microscope;
determining, via the processor, whether the optical module and the phase lamp are compatible based on the compatibility information; and
in response to a determination that the optical module and the phase lamp are incompatible, causing, via the processor, an alert to be displayed with an indication of incompatibility.

23. The method of claim 18, further comprising:
extending a shaft in a first orientation through an optical module of the fluorescence microscope to a receptacle in the fluorescence microscope; and rotating the shaft under the application of a force such that shaft moves to a second orientation thereby coupling the optical module to the fluorescence microscope.

24. A non-transitory computer-readable medium having stored thereon program instructions that upon execution by a processor in electro-mechanical communication with the system of claim 1, cause performance of a set of acts comprising:

aligning a first biological sample and a fluorescence microscope such that the first biological sample is located within a field of view of the fluorescence microscope, wherein the first biological sample contains (i) a first fluorophore that emits light in a first band of emission wavelengths in response to illumination by light in first band of excitation wavelengths, (ii) a second fluorophore that emits light in a second band of emission wavelengths in response to illumination by light in second band of excitation wavelengths, and (iii) a third fluorophore that emits light in a third band of emission wavelengths in response to illumination by light in third band of excitation wavelengths;

the imaging sensor obtaining a first set of images of the first biological sample using the fluorescent microscope, wherein the images of the set of images differ with respect to focus setting;

determining, based on the set of images, first, second, and third in-focus settings for the first, second, and third bands of emission wavelengths, respectively;

during a first period of time, using a first light source to illuminate the first biological sample with light in the first band of excitation wavelengths and operating the fluorescence microscope according to the first in-focus setting to obtain, via an image sensor of the fluorescence microscope, a first image of light in the first band of emission wavelengths;

during a second period of time, using a second light source to illuminate the first biological sample with light in the second band of excitation wavelengths and operating the fluorescence microscope according to the second in-focus setting to obtain, via the image sensor, a second image of light in the second band of emission wavelengths; and during a third period of time, using a third light source to illuminate the first biological sample with light in the third band of excitation wavelengths and operating the fluorescence microscope according to the third in-focus setting to obtain, via the image sensor, a third image of light in the third band of emission wavelengths.

* * * * *